US007192755B1

(12) United States Patent
Mori et al.

(10) Patent No.: US 7,192,755 B1
(45) Date of Patent: Mar. 20, 2007

(54) NICOTIANAMINE SYNTHASE AND GENE ENCODING THE SAME

(75) Inventors: Satoshi Mori, Chiba-ken (JP); Kyoko Higuchi, Gunma (JP); Kazuya Suzuki, Tokyo (JP); Naoko Nishizawa, Tokyo (JP); Hiromi Nakanishi, Tokyo (JP)

(73) Assignee: Japan Science and Technology Corporation, Saitama-Ken (JP)

( * ) Notice: Subject to any disclaimer, the term of this patent is extended or adjusted under 35 U.S.C. 154(b) by 0 days.

(21) Appl. No.: 09/674,337

(22) PCT Filed: Apr. 30, 1999

(86) PCT No.: PCT/JP99/02305

§ 371 (c)(1),
(2), (4) Date: Jul. 26, 2001

(87) PCT Pub. No.: WO99/57249

PCT Pub. Date: Nov. 11, 1999

(30) Foreign Application Priority Data

Apr. 30, 1998 (JP) ................................. 10-137685

(51) Int. Cl.
 C12N 9/10 (2006.01)
 C12N 9/00 (2006.01)
 A01H 9/00 (2006.01)
 A01H 5/00 (2006.01)
(52) U.S. Cl. ...................... 435/193; 435/183; 530/350; 800/295; 800/320; 800/320.2
(58) Field of Classification Search ................ 435/183, 435/193; 530/350; 800/295, 320, 320.2
See application file for complete search history.

(56) References Cited

FOREIGN PATENT DOCUMENTS

WO 99/60107 11/1999

OTHER PUBLICATIONS

Attwood et al. Which craft is best in bioinformatics? Comput. Chem. 2001, vol. 25(4), pp. 329-339.*
Ponting, C.P. Issues in predicting protein function from sequence. Brief. Bioinform. Mar. 2001, vol. 2(1), pp. 19-29.*
Accession Q9ZQV8.*
Higuchi et al. Plant Physiol. Feb. 1999;119(2):471-80.*
K. Higuchi et al., *Journal of Experimental Botony*, 46(289):1061-1063 (1995).
K. Higuchi et al., *Plant Soil*, 165:173-179 (1994).
K. Higuchi et al., *Plant Soil*, 178:171-177 (1996).
S. Mori, *Soil Science and Plant Nutrition*, 43:975-980 (1997).
H. Ling et al., *Molecular and General Genetics*, 252:87-92 (1996).
K. Higuchi et al., *Journal of Plant Nutrition*, 19(8-9):1235-1239 (1996).
Mori et al., *EMBL Nucleotide Sequence*, Accession No. AB010086 (1999).

Mori et al., *EMBL Nucleotide Sequence*, Accession No. AB011265 (1999).
Mori et al., *EMBL Nucleotide Sequence*, Accession No. AB011264 (1999).
Mori et al., *EMBL Nucleotide Sequence*, Accession No. AB011266 (1999).
Mori et al., *EMBL Nucleotide Sequence*, Accession No. AB011268 (1999).
Mori et al., *EMBL Nucleotide Sequence*, Accession No. AB011269 (1999).
Mori et al., *EMBL Nucleotide Sequence*, Accession No. AB019525 (1999).
Higuchi et al., *Plant Physiology, American Society of Plant Physiologists*, 119:471-479 (1999).
K. Suzuki et al., *Database EMBL Sequence Library*, Accession No. AB021935 (1999).
Plant and Soil, vol. 165, No. 2, issued 1994, Kyoko Higuchi et al.; Purification and characterization of nicotianamine synthase from Fe- deficient barley roots, pp. 173-179.
Plant Physiology, vol. 199, No. 2, issued Feb. 1999, Kyoko Higushi et al., Cloning of Nicotianamine Synthase Genes, Novel Genes Involved in the Biosynthesis of Phytosiderophores, pp. 417-479.
Database GenBank, Accession No. AB019525, Feb. 11, 1999, Mori S. "*Horedeum vulgare* hvnas7 mRNA for nicotianamine synthase 7, complete cds".
Database GenBank, Accession No. AB021746, Mar. 30, 1999, Mari S. "*Oryza sativa* osnasl mRNA for nicotianamine synthase 1, complete cds".
Database GenBank, Accession No. AB0211934, Feb. 11, 1999, Suzuki K. "*Arabidopsis thaliana* gene for nicotianamine synthase, complete cds."
Frances H. Arnold, "Design by Directed Evolution", Acc. Chem. Res., 31:125-131 (1998).
R.W. Old et al., Fourth Edition, Principles of Gene Manipulation, an Introduction to Genetic Engineering, Blackwell Scientific Publications, Studies in Microbiology vol 2, Chapter 4, pp. 75-98 (1980).
J. Sambrook et al., Molecular Cloning, A Laboratory Manual, Second Edition, Cold Spring Harbor Laboratory Press, "Generation of Deletions and Insertions", pp. 15.3-15.113 (1989).

* cited by examiner

*Primary Examiner*—Tekchand Saidha
*Assistant Examiner*—Christian L. Fronda
(74) *Attorney, Agent, or Firm*—Peter F. Corless; Jonathan M. Spaks; Edwards Angell Palmer and Dodge, LLP

(57) ABSTRACT

A nicotianamine synthase is isolated and purified. Then the gene of this enzyme is cloned and the base sequence and amino acid sequence thereof are determined. This gene is employed in constructing plants, in particular, grass plants highly tolerant to iron deficiency. A nicotianamine synthase involved in the mugineic acid biosynthesis pathway; the amino acid sequence thereof; a gene encoding the same; a vector containing this gene; cells transformed by the vector; a process for producing nicotianamine by using the same; plants transformed by the gene encoding the nicotianamine synthase; and an antibody against the nicotianamine syntase.

20 Claims, 18 Drawing Sheets

Fig. 5

```
33,32 kDa -1    DAQNKEVAALIEKIAGIQA
                ::: ::::: :: ::::::
rice (D24790)   MEAQNQEVAALVEKIAGLHAAISKLPSLSPSAEVDALFTDLVTACVPASPVDVAKLGPEAQAMREELIRLC
                NT primer →                                                   ← NR primer 33,32 kDa -2    REALIRL
                                                                                                          :::::::
rice (D23792)   YVNLSKLEYDLLVRYVPGIAPTRVAFVGSSGPLPFSSLVLAAHHLPDAVFDNYDRCGAANERARRLFRGADEGLGARM~
                            IF primer →
                ~AFHTGDVATLTGELGAYDVVFLATLVGMAAEEKP
                                        IR primer →
33,32 kDa -3    SFHTADVADLTQELGAYDVVFLAALVDMAAEEKAKVIAHLGAHMVEGASLVVYSAHGARGFLYP
                :::::::::::::::::::::: ::::::: :::
30 kDa -1       AFHTAEVTDLTAELGAYDV                        30 kDa -2    ADGAVLVARSAHGARAFLYPVVELDDVGR
                                                                       : :: ::::::::: :::::
33,32 kDa -4    PEDIRRGGFEVLAVHHPEGE
```

Fig. 6

```
      GCG TTC AGA GGC TTC CAG AGT TCT TCC GGT CAC CAA GAA GCA TTT GAT CAT AAC    54
      ATG GAT GCC CAG AAC AAG GAG GTC GCT GCT CTG ATC GAG AAG ATC GCC GGT ATC   108
 19   M   D   A   Q   N   K   E   V   A   A   L   I   E   K   I   A   G   I
          ①
      CAG GCC GCC ATC GCC GAG CTG CCG TCG CTG AGC CCG TCC CCC GAG GTC GAC AGG   162
 37   Q   A   A   I   A   E   L   P   S   L   S   P   S   P   E   V   D   R

CTC TTC ACC GAC CTC GTC ACG GCC TGC GTC CCG CCG AGC CCC GTC GAC GTG ACG   216
 55   L   F   T   D   L   V   T   A   C   V   P   P   S   P   V   D   V   T

AAG CTC AGC CCG GAG CAC CAG AGG ATG CGG GAG GCT CTC ATC CGC TTG TGC TCC   270
 73   K   L   S   P   E   H   Q   R   M   R   E   A   L   I   R   L   C   S
                                          ②
      GCC GCC GAG GGG AAG CTC GAG GCG CAC TAC GCC GAC CTG CTC GCC ACC TTC GAC   324
 91   A   A   E   G   K   L   E   A   H   Y   A   D   L   L   A   T   F   D

AAC CCG CTC GAC CAC CTC GGC CTC TTC CCG TAC TAC AGC AAC TAC GTC AAC CTC   378
109   N   P   L   D   H   L   G   L   F   P   Y   Y   S   N   Y   V   N   L

AGC AGG CTG GAG TAC GAG CTC CTG GCG CGC CAC GTG CCG GGC ATC GCG CCG GCG   432
127   S   R   L   E   Y   E   L   L   A   R   H   V   P   G   I   A   P   A

CGC GTC GCC TTC GTC GGC TCC GGC CCG CTG CCG TTC AGC TCG CTC GTC CTC GCC   486
145   R   V   A   F   V   G   S   G   P   L   P   F   S   S   L   V   L   A

GCG CAC CAC CTG CCC GAG ACC CAG TTC GAC AAC TAC GAC CTG TGC GGC GCG GCC   540
163   A   H   H   L   P   E   T   Q   F   D   N   Y   D   L   C   G   A   A

AAC GAG CGC GCC AGG AAG CTG TTC GGC GCG ACG GCG GAC GGC GTC GGC GCG CGT   594
181   N   E   R   A   R   K   L   F   G   A   T   A   D   G   V   G   A   R

ATG TCG TTC CAC ACG GCG GAC GTC GCC GAC CTC ACC CAG GAG CTC GGC GCC TAC   648
199   M   S   F   H   T   A   D   V   A   D   L   T   Q   E   L   G   A   Y
          ③
      GAC GTG GTC TTC CTC GCC GCG CTC GTC GGC ATG GCA GCC GAG GAG AAG GCC AAG   702
217   D   V   V   F   L   A   A   L   V   G   M   A   A   E   E   K   A   K

GTG ATT GCC CAC CTG GGC GCG CAC ATG GTG GAG GGG GCG TCC CTG GTC GTG CGG   756
235   V   I   A   H   L   G   A   H   M   V   E   G   A   S   L   V   V   R

AGC GCA CGG CCC CGC GGC TTT CTT TAC CCC ATT GTC GAC CCG GAG GAC ATC AGG   810
253   S   A   R   P   R   G   F   L   Y   P   I   V   D   P   E   D   I   R
                                                              ④
      CGG GGT GGG TTC GAG GTG CTG GCC GTG CAC CAC CCG GAA GGT GAG GTG ATC AAC   864
271   R   G   G   F   E   V   L   A   V   H   H   P   E   G   E   V   I   N

TCT GTC ATC GTC GCC CGT AAG GCC GTC GAA GCG CAG CTC AGT GGG CCG CAG AAC   918
289   S   V   I   V   A   R   K   A   V   E   A   Q   L   S   G   P   Q   N

GGA GAC GCG CAC GCA CGG GGC GCG GTG CCG TTG GTC AGC CCG CCA TGC AAC TTC   972
307   G   D   A   H   A   R   G   A   V   P   L   V   S   P   P   C   N   F

TCC ACC AAG ATG GAG GCG AGC GCG CTT GAG AAG AGC GAG GAG CTG ACC GCC AAA  1026
325   S   T   K   M   E   A   S   A   L   E   K   S   E   E   L   T   A   K

GAG CTG GCC TTT TGA TTG AAG AGT GCG CGT GGT CAT TCT GTC GCC TGC GAT CGT  1080
      E   L   A   F   *

GGT AAC TTT CCT ACT CGT GTG TGT TTT GAT GTT TGT GCC TGT AAG AGT TAT GCT  1134
      TCC GGC CTT GTG CTG TTA ATT TAC ACG CGT TAC ATG TAG TAC TTG TAT TTA TAC  1188
      CTG GAA TAA CGG TAT GTA ACA TAA ATA TTA GTG GGA TTT GAA GTG TAA TGC TAA  1242
      ATA ATA AGA AAA CTT GAT GCA GAC ATT CAA AAA AAA AAA AAA AAA AAA AAA AA
```

Fig. 7

| | |
|---|---|
| HvNAS4 | MDGQSE--EVDALVQKITGLHAAIAKLPSLSPSPDVDALFTDLVTACVPPSPVDVTKLAP |
| HvNAS7 | MDAQSK--EVDALVQKITGLHAAIAKLPSLSPSPDVDALFTDLVTACVPPSPVDVTKLAP |
| HvNAS6 | MDAQNK--EVDALVQKITGLHAAIAKLPSLSPSPDVDALFTDLVTACVPPSPVDVTKLGS |
| HvNAS2 | MAAQNN-QEVDALVEKITGLHAAIAKLPSLSPSPDVDALFTELVTACVPPSPVDVTKLGP |
| HvNAS3 | MAAQNNNKDVAALVEKITGLHAAIAKLPSLSPSPDVDALFTELVTACVPPSPVDVTKLGP |
| HvNAS1 | MDAQNK--EVAALIEKIAGIQAAIAELPSLSPSPEVDRLFTDLVTACVPPSPVDVTKLSP |
| HvNAS5 | MEAENG--EVAALVEKITGLHAAISKLPALSPSPQVDALFTELVAACVPSSPVDVTKLGP |
| | *   **  **  *  ***  **  *****  **  *** ** ****  ******** |

| | |
|---|---|
| HvNAS4 | EAQAMREGLIRLCSEAEGKLEAHYSDMLAAFDNPLDHLGVFPYYSNYINLSKLEYELLAR |
| HvNAS7 | EAQAMREGLIRLCSEAEGKLEAHYSDMLAAFDNPLDHLGVFPYYSNYINLSKLEYELLAR |
| HvNAS6 | EAQEMREGLIRLCSEAEGKLEAHYSDMLAAFDNPLDHLGMFPYYSNYINLSKLEYELLAR |
| HvNAS2 | EAQEMREGLIRLCSEAEGKLEAHYSDMLAAFDKPLDHLGMFPYYNNYINLSKLEYELLAR |
| HvNAS3 | EAQEMREGLIRLCSEAEGKLEAHYSDMLAAFDNPLDHLGIFPYYSNYINLSKLEYELLAR |
| HvNAS1 | EHQRMREALIRLCSAAEGKLEAHYADLLATFDNPLDHLGLFPYYSNYVNLSRLEYELLAR |
| HvNAS5 | EAQEMRQDLIRLCSAAEGLLEAHYSDMLTALDSPLDHLGRFPYFDNYVNLSKLEHDLLAG |
| | *  * **  ****** *** *****  *   *  ******  ***  ** ***  ** *** |

| | |
|---|---|
| HvNAS4 | YVPGRHRPARVAFIGSGPLPFSSYVLAARHLPDTVFDNYDLCGAANDRATRLFRADKD-V |
| HvNAS7 | YVPGGIAPARVAFIGSGPLPFSSYVLAARHLPDTVFDNYVPVRAANDRATRLFRADKD-V |
| HvNAS6 | YVPGGIARPAVAFIGSGPLPFSSYVLAARHLPDAMFDNYDLCSAANDRASKLFRADKD-V |
| HvNAS2 | YVPGGYRPARVAFIGSGPLPFSSFVLAARHLPDTMFDNYDLCGAANDRASKLFRADRD-V |
| HvNAS3 | YVRR-HRPARVAFIGSGPLPFSSFVLAARHLPDTMFDNYDLCGAANDRASKLFRADTD-V |
| HvNAS1 | HVPG-IAPARVAFVGSGPLPFSSLVLAAHHLPETQFDNYDLCGAANERARKLFGATADGV |
| HvNAS5 | HVAA---PARVAFIGSGPLPFSSLFLATYHLPDTRFDNYDRCSVANGRAMKLVGAADEGV |
| | *      ***  ********  **  ***   ****    **  **  *  *     * |

| | |
|---|---|
| HvNAS4 | GARMSFHTADVADLTDELATYDVVFLAALVGMAAEDKAKVIAHLGAHMADGAALV--ARH |
| HvNAS7 | GARMSFHTADVADLTDELATYDVVFLAALVGMAAEDKGQGDPHLGAHMADGAALVR-SAH |
| HvNAS6 | GARMSFHTADVADLTRELAAYDVVFLAALVGMAAEDKAKVIPHLGAHMADGAALVV-RSA |
| HvNAS2 | GARMSFHTADVADLAGELAKYDVVFLAALVGMAAEDKAKVIAHLGAHMADGAALVVRSAH |
| HvNAS3 | GARMSFHTADVADLASELAKYDVVFLAALVGMAAEDKAKVIAHLGAHMADGAALVVRSAH |
| HvNAS1 | GARMSFHTADVADLTQELGAYDVVFLAALVGMAAEEKAKVIAHLGAHMVEGASLVV-RSA |
| HvNAS5 | RSRMAFHTAEVTDLTAELGAYDVVFLAALVGMTSKEKADAIAHLGKHMADGAVLVREALH |
| | ** ****  *  **   **  ***********    *     *** **  **  ** |

| | |
|---|---|
| HvNAS4 | GARGFLYPIVDPQDIGRGGFEVLAVCHPD-DDVVNSVIIAQKSNDVHEYGLGSGR--GGR |
| HvNAS7 | GARGFLYPIVDPQDIGRGGFEVLAVCHPD-DDVVNSVIIAQKSKDMFANGPRNGC--GGR |
| HvNAS6 | QARGFLYPIVDPQDIGRGGFEVLAVCHPD-DDVVNSVIIAHKSKDVHANERPNGR--GGQ |
| HvNAS2 | GARGFLYPIVDPQDIGRGGFEVLAVCHPD-DDVVNSVIIAQKSKDVHADGLGSGRGAGGQ |
| HvNAS3 | GARGFLYPIVDPQDIGRGGFEVLAVCHPD-DDVVNSVIIAQKSKEVHADGLGSARGAGRQ |
| HvNAS1 | RPRGFLYPIVDPEDIRRGGFEVLAVHHPE-GEVINSVIVARKAVEAQLSGPQNGD----A |
| HvNAS5 | GARAFLYPVVELDDVGRGGFQVLAVHHPAGDEVFNSFIVARKVKMSA------------- |
| | *  ****  *   *  **** ****  **    *  ** * * * |

| | |
|---|---|
| HvNAS4 | YARGTVVPVVSPPCRFG-EMVADVTQ--KREEFANAEVAF |
| HvNAS7 | YARG-TVPVVSPPCRFG-EMVADVTQ--KREEFAKAEVAF |
| HvNAS6 | YRGA--VPVVSPPCRFG-EMVADVTH--KREEFTNAEVAF |
| HvNAS2 | YARG-TVPVVSPPCRFG-EMVADVTQNHKRDEFANAEVAF |
| HvNAS3 | YARG-TVPVVSPPCRFG-EMVADVTQNHKRDEFANAEVAF |
| HvNAS1 | HARG-AVPLVSPPCNFSTKMEASALE--KSEELTAKELAF |
| | ** ***** *  * *         *  *  * ** |

Fig. 12
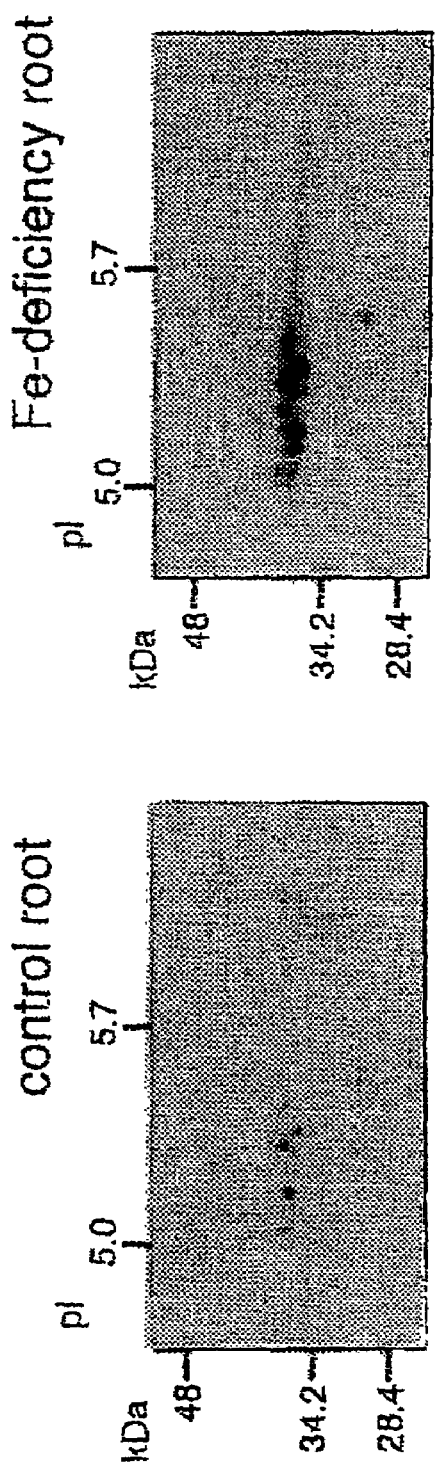
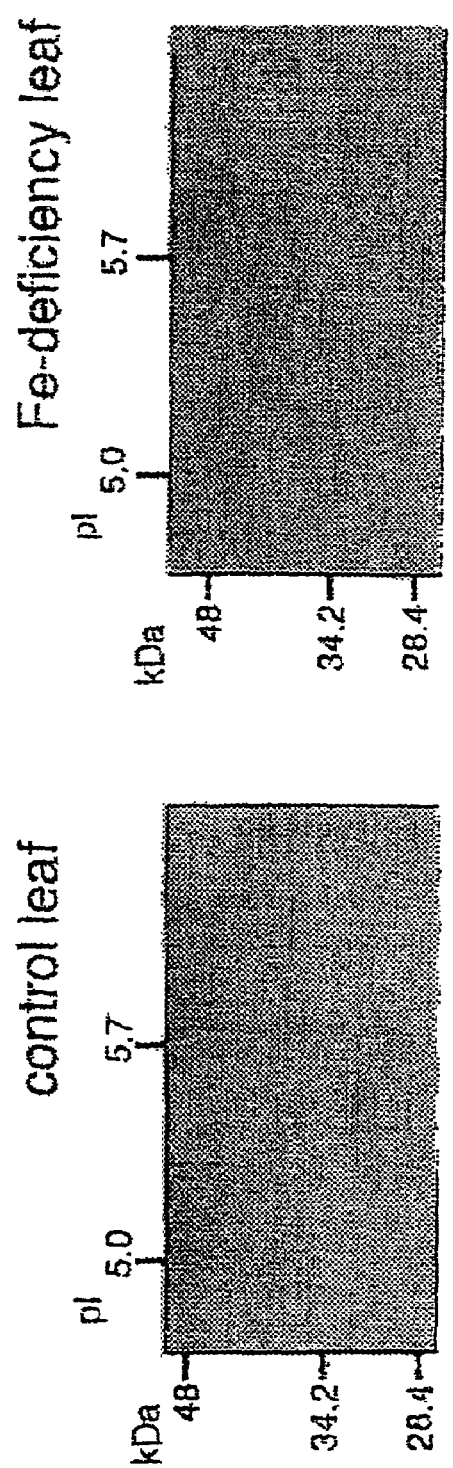

ly NICOTIANAMINE SYNTHASE AND GENE ENCODING THE SAME

TECHNICAL FIELD

The present invention relates to a nicotianamine synthase involved in the mugineic acid biosynthetic pathway, the amino acid sequence thereof, a gene encoding the same, a vector, a process for producing nicotianamine by using the same, plants transformed by the gene encoding the nicotianamine synthase, and an antibody against the nicotianamine synthase.

BACKGROUND ART

Graminaceous plants that absorb by chelating the insoluble state Fe(III) in soil using mugineic acid and adopt so called the Strategy-II mechanism of Fe acquisition secrete Fe chelators (phytosiderophores) from their roots to solubilize sparingly soluble Fe in the rhizosphere (Roemheld, 1987). The amount of the secreted phytosiderophores increases under Fe-deficiency stress. The mugineic acid family is the only examples of phytosiderophores known so far (Takagi, 1976). Tolerance to Fe deficiency in graminaceous plants is thought to depend on a quantity of mugineic acid family secreted by plants (Takagi et al. 1984, Roemheld and Marschner 1986, Marschner et al. 1987, Mori et al. 1987, Kawai et al. 1988, Mori et al. 1988, Mihashi and Mori 1989, and Shingh et al. 1993).

The biosynthetic pathway of mugineic acid in plants is shown in FIG. 1. S-adenosylmethionine is synthesized from methionine by S-adenosylmethionine synthase. Subsequently, three molecules of S-adenosylmethionine are combined to form one molecule of nicotianamine by nicotianamine synthase. The generated nicotianamine is then converted to 3"-keto acid by nicotianamine aminotransferase, and 2'-deoxymugineic acid is synthesized by the subsequent action of a reductase. A further series of hydroxylation steps produces the other mugineic acid derivatives including mugineic acid from the deoxymugineic acid (Mori and Nishizawa 1987, Shojima et al. 1989, Shojima et al. 1990 and Ma and Nomoto 1993).

A compound in FIG. 1, a compound in the lower right, wherein $R_1$ and $R_2$ are hydrogen and $R_3$ is hydroxyl, is mugineic acid. A compound wherein $R_1$ is hydrogen and $R_2$ and $R_3$ are hydroxyl, is 3-hydroxymugineic acid. Also a compound wherein $R_2$ is hydrogen and $R_1$ and $R_8$ are hydroxyl, is 3-epihydroxymugineic acid.

Three S-adenosylmethionine synthase genes were isolated from barley roots, but these genes were not induced by Fe deficiency (Takizawa et al. 1996). A gene Ids3, which is obtained from the barley by differential screening, is suspected to be a gene, which converts deoxymugineic acid to mugineic acid by hydroxylation and is strongly induced by Fe-deficiency (Nakanishi et al. 1993). Further, nicotianamine aminotransferase was purified and isolated from Fe-deficient barley roots, and two nicotianamine aminotransferase genes, Naat-A and Naat-B, were isolated (Takahashi et al. 1997). Naat-A expression was induced in Fe-deficient roots.

The synthesis of nicotianamine from S-adenosylmethionine is similar to polyamine synthesis from decarboxy-S-adenosylmethionine. In contrast to polyamine synthase, however, nicotianamine synthase catalyzes the combination of three S-adenosylmethionine molecules and the azetidine ring formation at the same time (FIG. 1). Such the nicotianamine synthase is a novel type of enzyme. Previously, we reported the partial purification of nicotianamine synthase from the roots of Fe-deficient barley and expression pattern of the activity (Higuchi et al. 1994, Higuchi et al. 1995, Kanazawa et al. 1995, Higuchi et al. 1996a and Higuchi et al. 1996b). Since nicotianamine synthase is easily decomposed during extraction and purification, it has been difficult to purify sufficient quantities for amino acid sequencing.

The present invention has an object to provide a plant, especially graminaceous plant, highly tolerant to Fe-deficiency, as a result of isolating and purifying a nicotianamine synthase, being cloned the gene of this enzyme, determining the base sequence and amino acid sequence thereof, and using said enzyme.

DISCLOSURE OF INVENTION

The present invention relates to a nicotianamine synthase shown in SEQ ID NO: 1 comprising amino acid sequence shown in SEQ ID NO: 1, or amino acid sequence having deletion in a part thereof, being substituted by the other amino acids or being added with the other amino acids.

The present invention relates to the gene encoding said amino acid sequence of nicotianamine synthase.

The present invention also relates to a vector comprising containing said gene, and a transformant transformed by the said vector.

The present invention relates to a process for production of nicotianamine using the said transformant.

The present invention further relates to plants, especially graminaceous plants, to which said gene is introduced, and fruits obtained by growing said plants.

The present invention relates to a process for extraction of said nicotianamine synthase in the presence of thiol protease inhibitor, preferably E-64.

Further, the present invention relates to an antibody against said nicotianamine synthase.

The large closed circles (●) indicates enzyme activity.

FIG. 5 shows a comparison with a six partial amino acid sequence determined by nicotianamine synthase originated from barley and similar sequence of graminaceous plants obtained by computer search of the database. Identical amino acid residue is shown in ":" (SEQ ID NOS 30–37, respectively in order of appearance).

FIG. 6 shows full length of HvNAS1 cDNA (SEQ ID NO: 2) and amino acid sequence (SEQ ID NO: 1) deduced therefrom. The underlined sequences indicate the identical partial amino acid sequences of fragments in the above FIG. 5. Numbers of the nucleotide sequence are indicated to the right of each row. Amino acid numbers are indicated on the left of each row.

FIG. 7 shows comparison of the deduced amino acid sequences of the above 7 cDNA obtained from barley (SEQ ID NOS 7, 13, 11, 3, 5, 1, and 9, respectively in order of appearance). Asterisks "*" indicates identical amino acid residues in all sequences used to generate consensus sequences SEQ ID NOS: 23–29.

Figure 8:
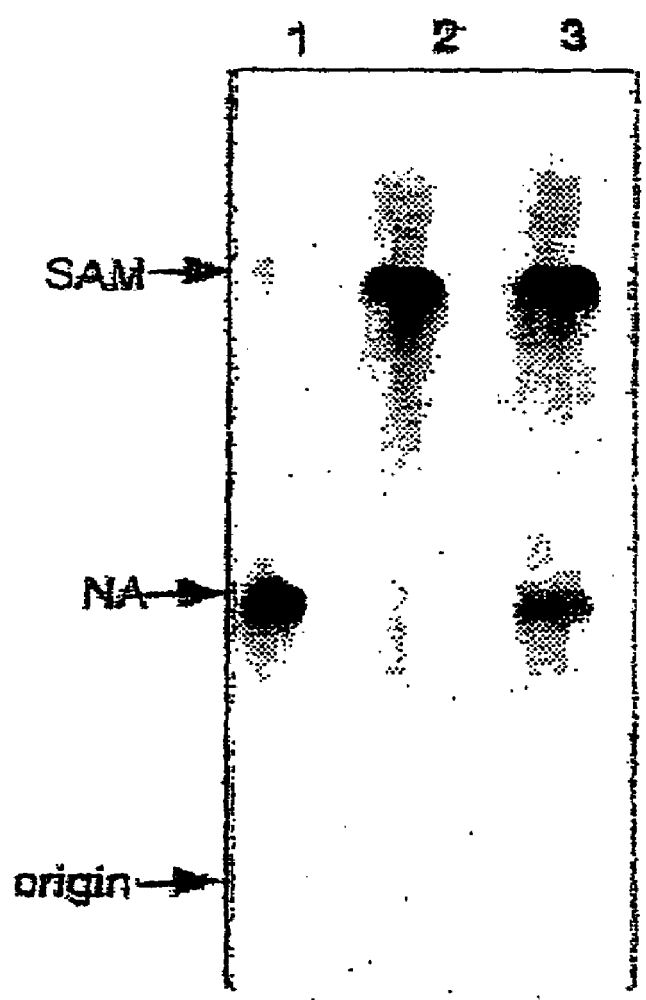

FIG. 8 shows results of thin layer chromatographic (TLC) analysis of nicotianamine synthase activity obtained from *E. coli* crude extract expressing a fused protein of maltose binding protein—HvNAS1.

Figure 9:
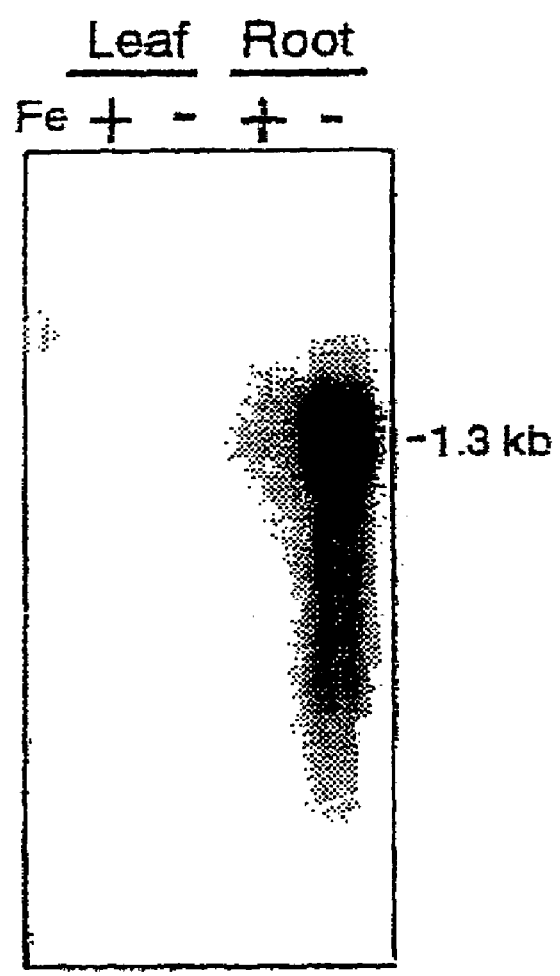

FIG. 9 shows Northern—hybridization analysis of HvNAS1 as a probe.

Figure 10:
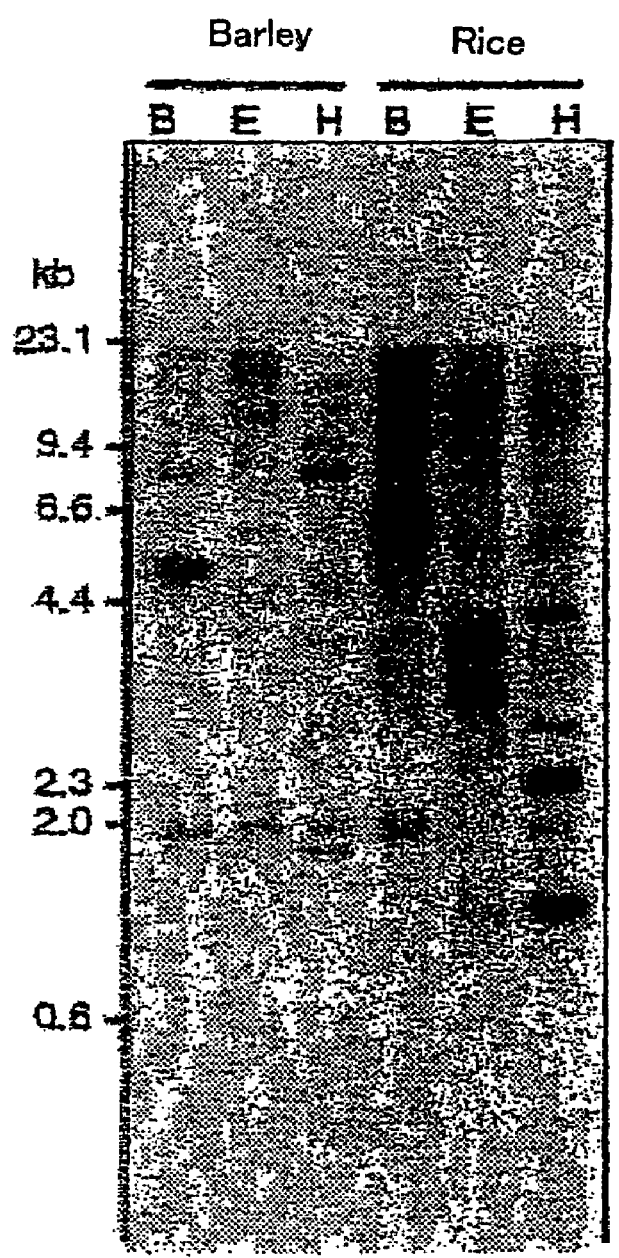

FIG. 10 shows Southern—hybridization analysis of HvNAS1 as a probe.

Figure 11:
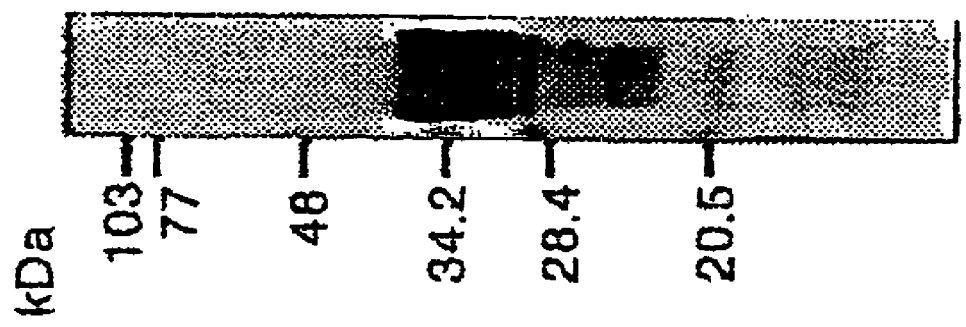

FIG. 11 shows Western-blot analysis of crude enzyme used for detection of nicotianamine synthase activity.

FIG. 12 shows Western-blot analysis of total protein extracted by trichloroacetic acid/acetone.

Figure 13:
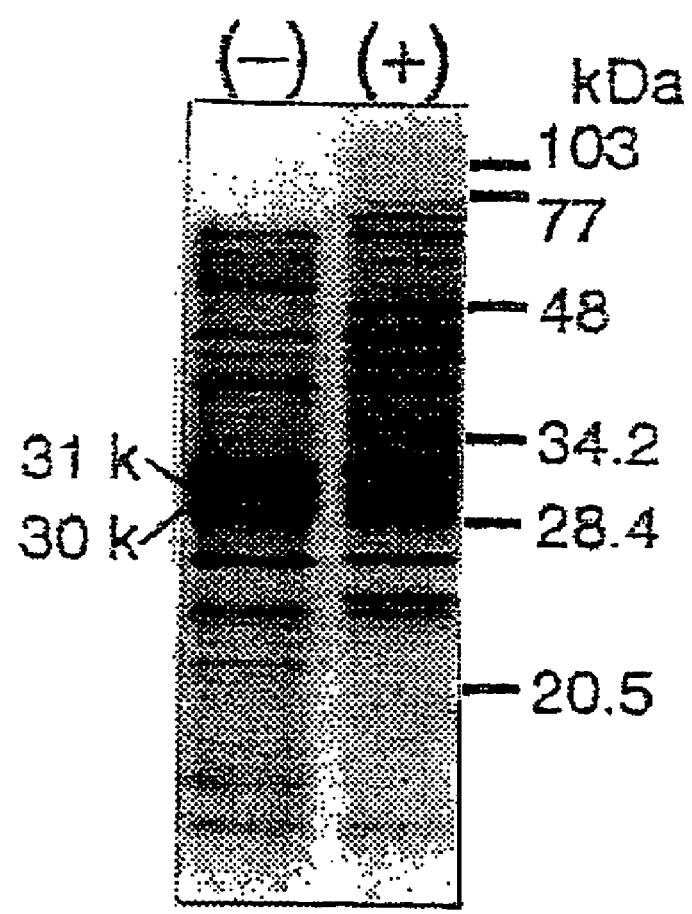

FIG. 13 shows comparison of nicotianamine synthase purification from Fe-deficient barley and control barley after DEAE-Sepharose FF.

Figure 14:
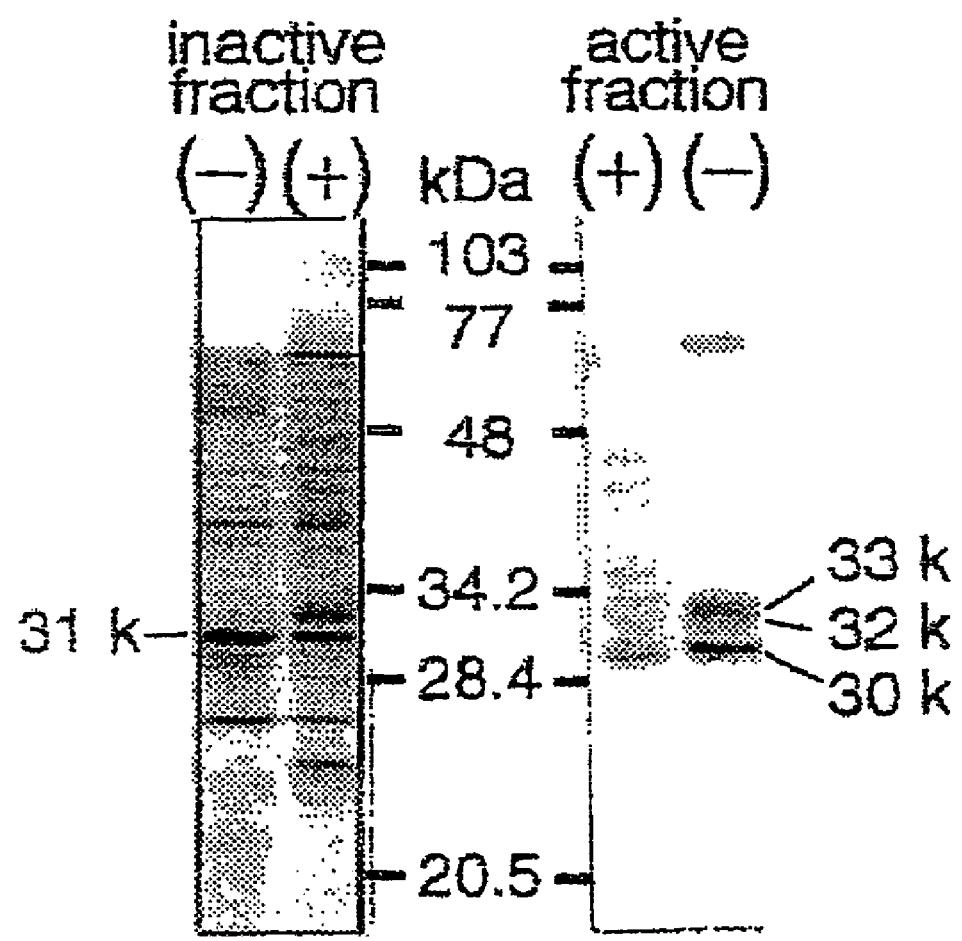

FIG. 14 shows comparison of nicotianamine synthase purification from Fe-deficient barley and control barley after Ether Toyopearl 650M.

Figure 15:
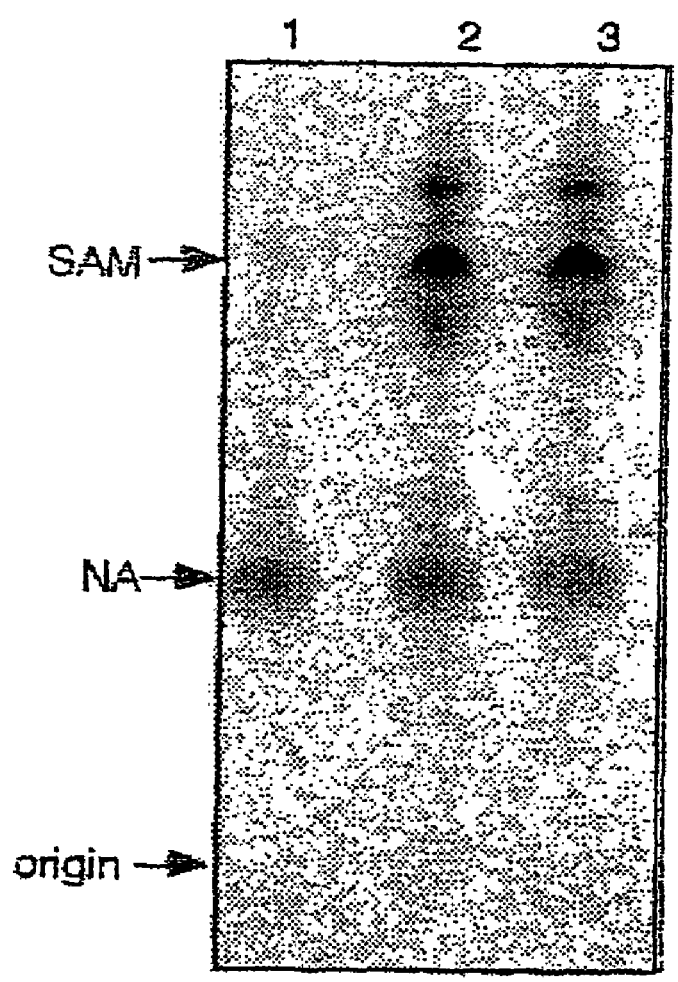

FIG. 15 shows results of thin layer chromatographic (TLC) analysis of nicotianamine synthase activity obtained from *E. coli* crude extract expressing a fused protein of maltose binding protein—OsNAS1.

Figure 16:
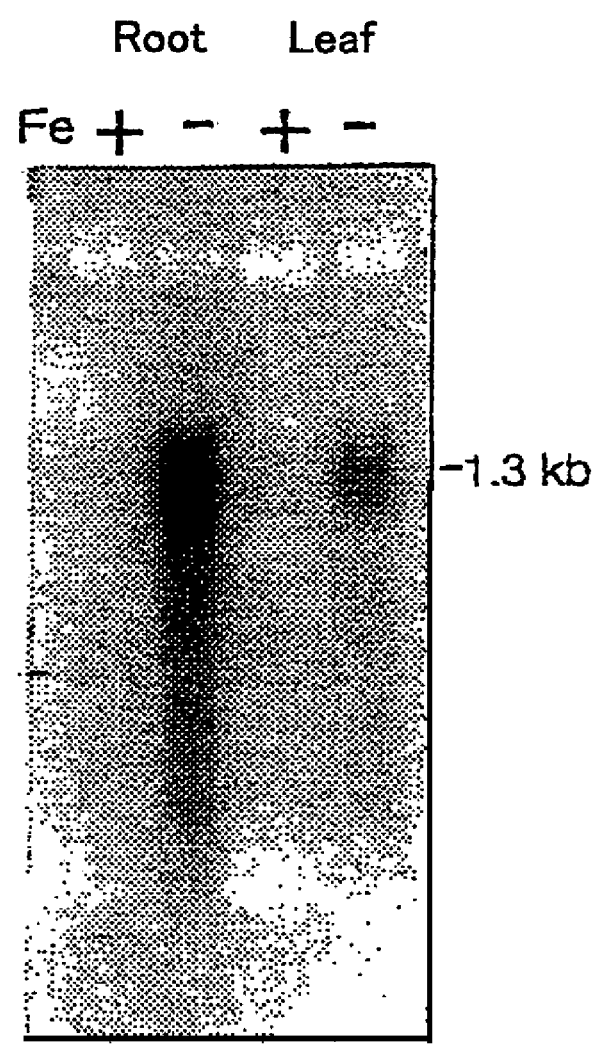

FIG. 16 shows Northern—hybridization analysis of OsNAS1 as a probe.

Figure 17:
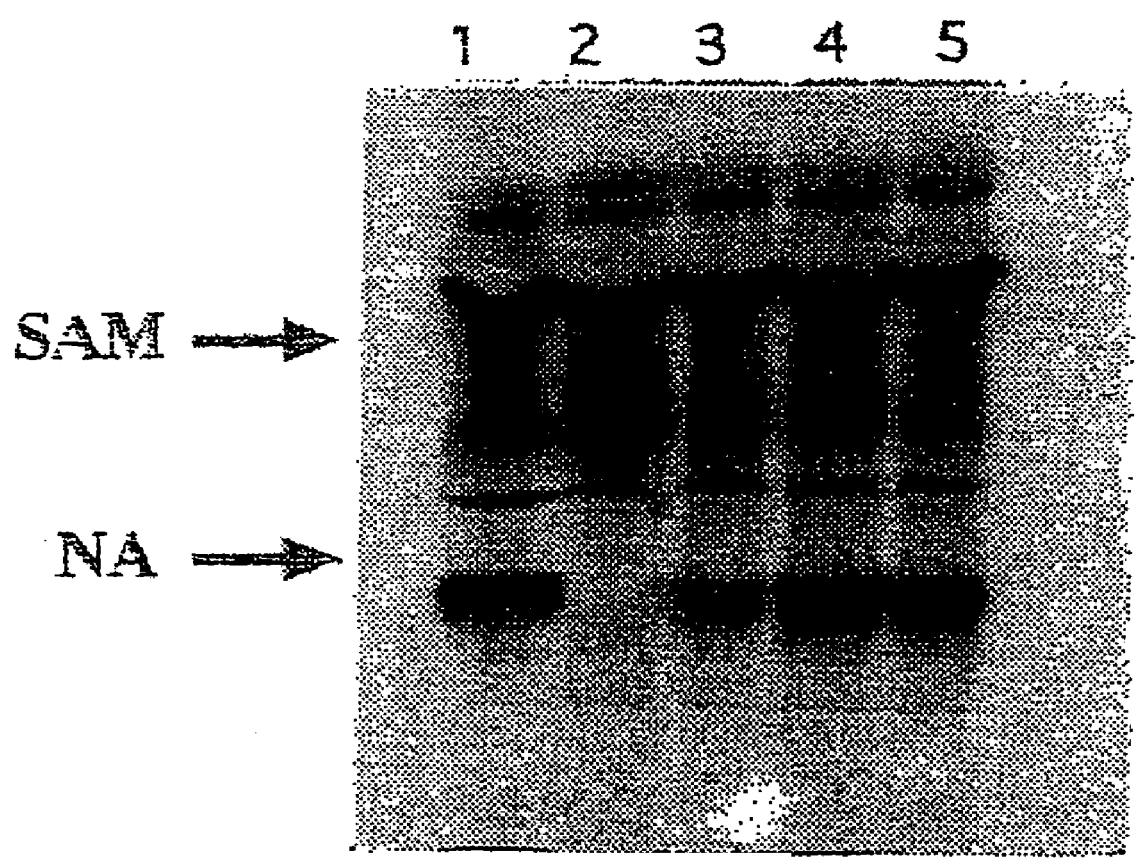

FIG. 17 shows results of thin layer chromatographic (TLC) analysis of nicotianamine synthase activity obtained from *E. coli* crude extract expressing a fused proteins of maltose binding protein—AtNAS1, AtNAS2 or AtNAS3.

Figure 18:
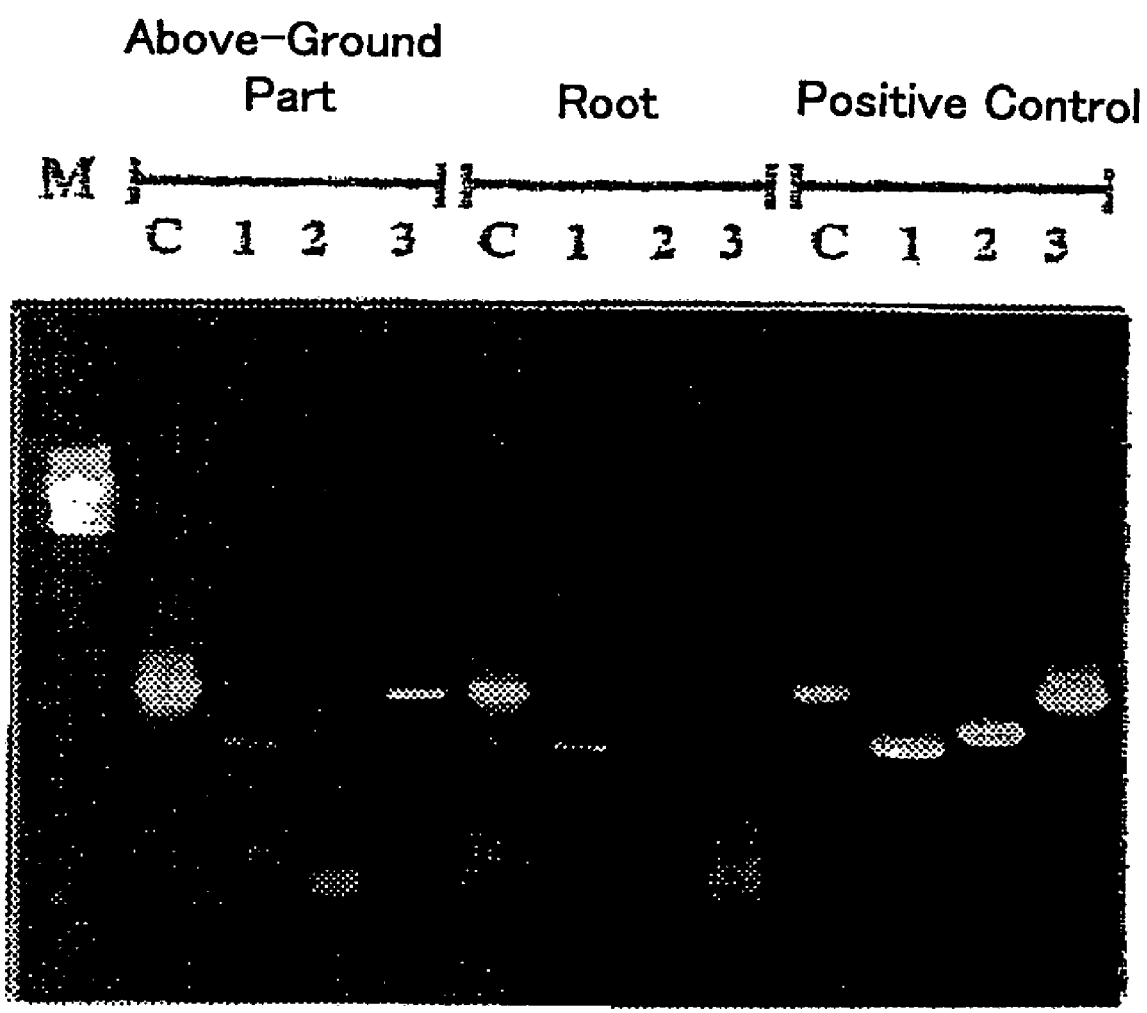

FIG. 18 shows results of RT-PCR of total RNA extracted from the aboveground parts and roots of *Arabidopsis thaliana*. Right group indicates positive control.

BEST MODE FOR CARRYING OUT THE INVENTION

We have tried to isolate nicotianamine synthase (Higuchi et al. Plant & Soil, Vol. 165, p. 173–179, 1994), and since nicotianamine synthase was easily decomposed and was difficult to isolate and purify, we were unable to obtain sufficient amounts of protein to determine its partial amino acid sequence. Subsequently, it was found that a thiol protease inhibitor E-64 (hereinafter designates as E-64) was very effective in suppressing degradation of nicotianamine synthase (Higuchi et al. Plant & Soil, Vol. 178, p. 171–177, 1996 a).

In the present invention, as a result that frozen roots were crushed to a fine powder in liquid $N_2$ and then rapidly homogenized with buffer containing 0.1 mM thiol protease inhibitor E-64, nicotianamine synthase protein could be isolated and its gene could also be isolated.

Further, the enzyme of the present invention recovered its activity by removal of SDS after SDS-PAGE treatment, but the rate of recovery was very low (Higuchi et al. Plant & Soil, Vol. 165, p. 173–179, 1994). Consequently, degree of purification should be increased up before treatment of SDS-PAGE. Then the column chromatography procedures were further improved.

We have also found that the enzyme of the present invention is relatively hydrophobic and a buffer containing a mild surface active agent CHAPS increased the rate of recovery. Several ion-exchange chromatography carriers were tested, and DEAE-Sepharose FF and DEAE Sephacel were found to be the most effective. In addition to TSK gel Butyl Toyopearl, another hydrophobic chromatography carrier, TSK gel Ether Toyopearl 650M, effectively removed impurities of the 30–35 kDa.

Figure 3:
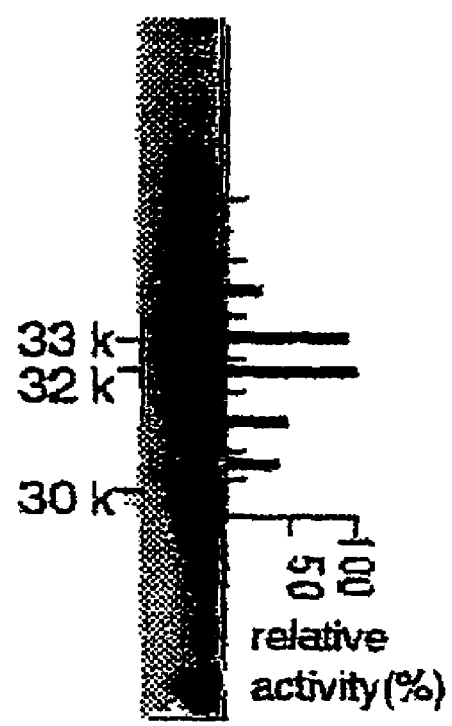
FIG. 3 shows a preparative SDS-PAGE (sodium dodecyl sulfate-polyacrylamide gel electrophoresis, hereinafter designates as SDS-PAGE) around 30–35 kDa. The horizontal bar indicates relative enzyme activity detected from the gels.

The enzyme of the present invention has been reported that it was the peptide of 30–35 kDa, the activity of which was recovered by removing SDS after SDS-PAGE treatment, and the activity was detected as a broad molecular weight range of 30–35 kDa (refer to FIG. 3). FIG. 3 shows a result of preparative SDS-PAGE in the fractions showing enzyme activity. SDS-PAGE was carried out using 11% acrylamide slab gels. A portion of the gel was stained with Coomassie brilliant blue and the rest of the gel was stained with Cu. The gel containing proteins between 30–35 kDa in size was cut into seven fragments (indicated by the short lines). The thick bars in FIG. 3 indicate relative enzymatic activities detected from each gel fragment.

In order to identify nicotianamine synthase peptide from the proteins having these molecular weights, the peptides, which were contained in the nicotianamine synthase fractions, purified from Fe-deficient and control barley roots were compared using SDS-PAGE. From each barley root 200 g, the present enzyme was purified according to the method described in example 3 hereinbelow.

The enzyme activity of the control was a quarter of the Fe-deficient roots.

Figure 1:
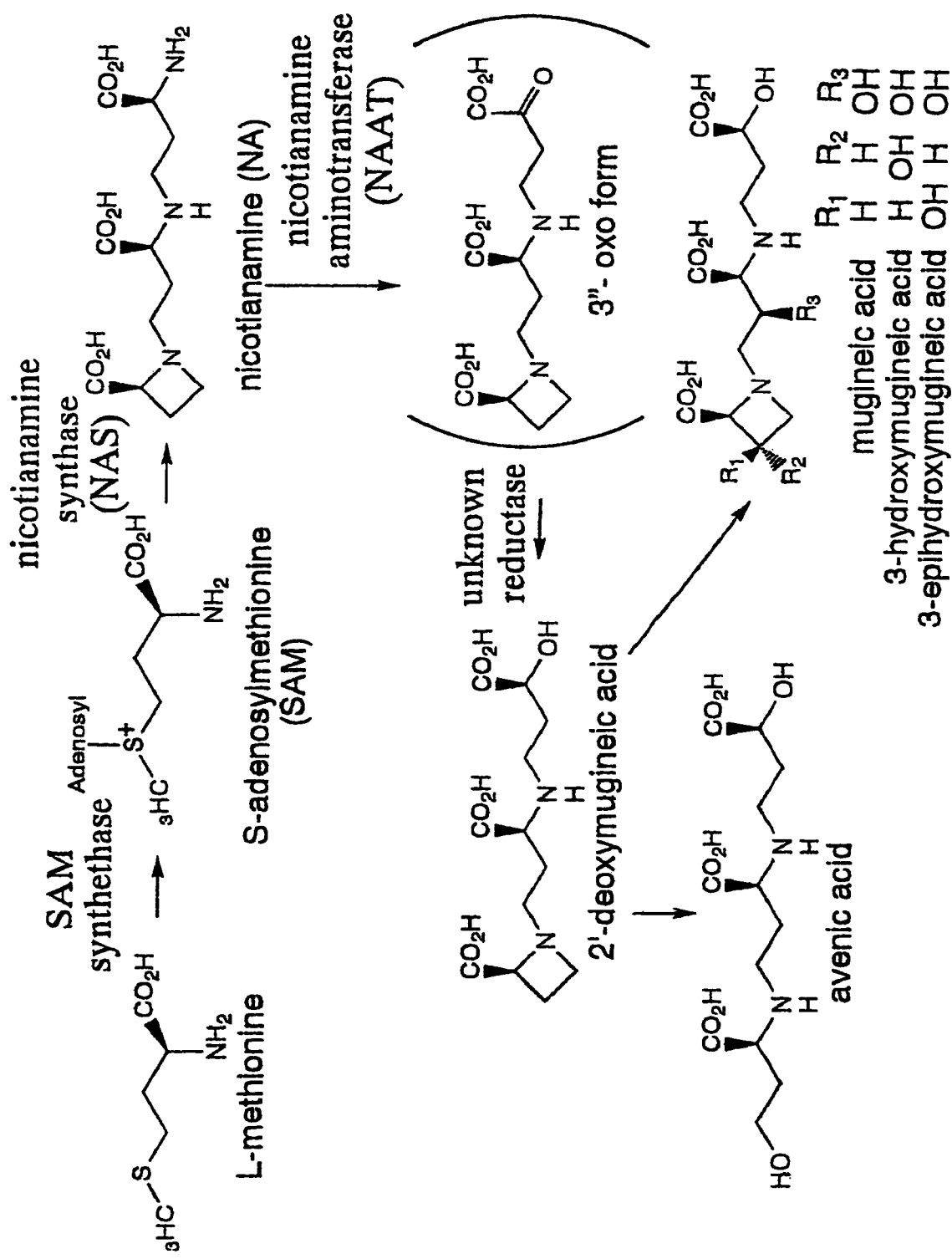
FIG. 1 shows the biosynthetic pathway of mugineic acid family.
Figure 2:
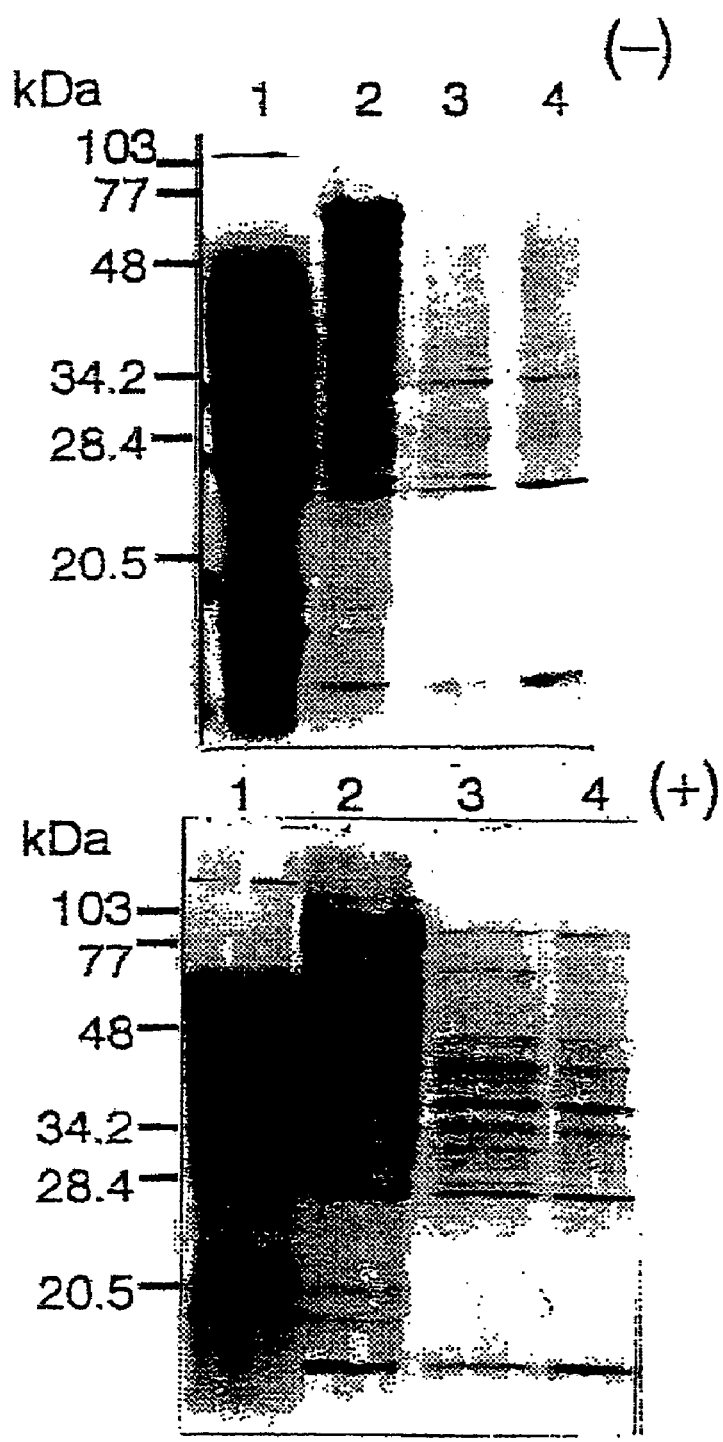
FIG. 2 shows a comparison of nicotianamine synthase purification from Fe-dependent and control barley roots.

The peptide composition of the active enzyme fraction from each purification step of the present enzyme was analyzed and compared by SDS-PAGE, and results are shown in FIG. 2, FIG. 13 and FIG. 14. FIG. 2, FIG. 13 and FIG. 14 show comparison with the active fraction from the purification step of Fe-deficient barley roots 200 g [in the figure, shown with (−)], and the active fraction from the purification step of the control barley roots 200 g [in the figure, shown with (+)]. SDS-PAGE was carried out using 12.5% acrylamide slab gels (Laemmli, Nature Vol. 227, p. 680–685, 1970). Gels were stained with Coomassie brilliant blue. FIG. 2 shows a step before DEAE-Sepharose. The upper row shows enzyme from Fe-deficient barley roots and the lower row shows enzyme from control roots. In each lane, lanes 1, crude extract, 200 μg of protein; lanes 2, after Butyl Toyopearl 650M, 100 μg of protein; lanes 3, after hydroxyapatite, 20 μg of protein; and lanes 4, after Butyl Toyopearl 650M, 15 μg of protein, are shown.

FIG. 13 shows after DEAE-Sepharose FF, each lane, 25 μg of protein. FIG. 14 shows after Ether Toyopearl 650M; in which left shows inactive fraction, and right shows active fraction, and ⅕ of each fraction is electrophoresed.

As a result, almost no difference was observed in both Fe-deficient and control roots before DEAE-Sepharose step (refer to FIG. 2). After the DEAE-Sepharose step it became clear that the 30- and 31-kDa peptides were induced by Fe-deficiency (refer to FIG. 13). After the Ether Toyopearl step, the 31 kDa peptide was eliminated from the active fraction. The 32 and 33 kDa peptides were found to be newly induced by Fe-deficiency (refer to FIG. 14). Activities were detected from the 32 and 33 kDa peptides, but no activity was detected from 30 kDa peptide (refer to FIG. 3).

Molecular weight of the enzyme of the present invention was determined by gel-filtration.

Estimated molecular weight of nicotianamine synthase by gel-filtration was reported to be 40,000–50,000 (Higuchi et al. Plant & Soil, Vol. 165, p. 173–179, 1994). But this did not correspond with the value estimated by SDS-PAGE.

Figure 4:
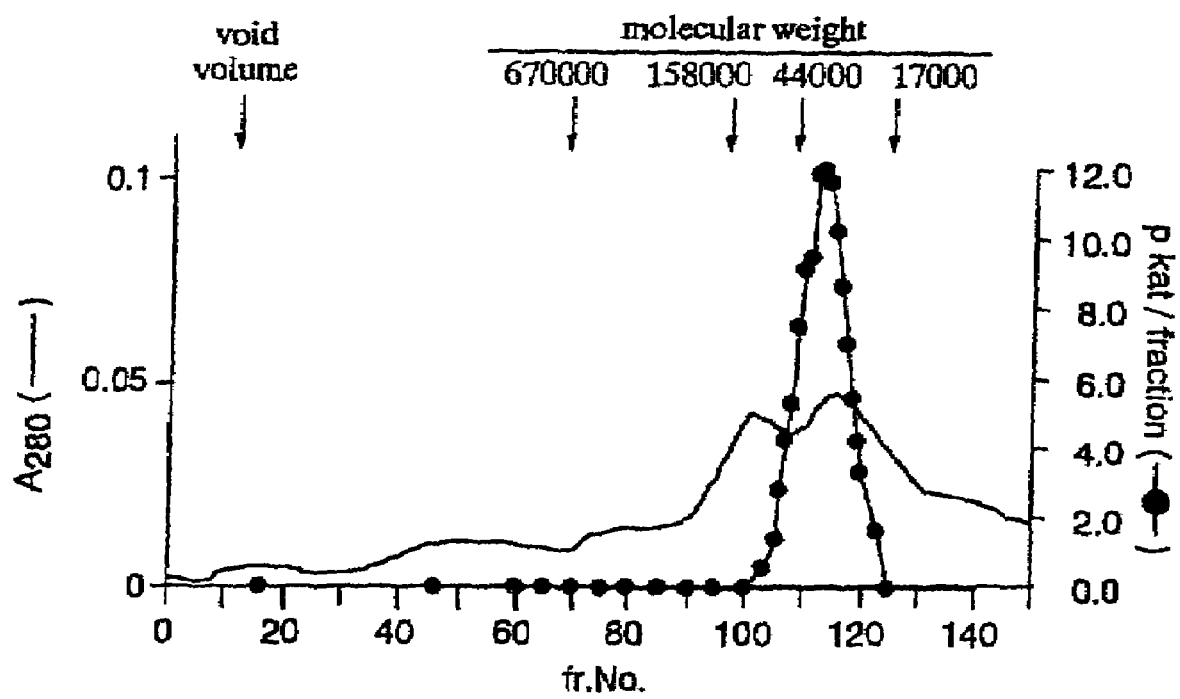
FIG. 4 shows elution pattern of nicotianamine synthase activity from the gel-filtration column.

In the present study, the buffer containing CHAPS effectively increased the resolution and molecular weight of the present enzyme was estimated to be 35,000 (refer to FIG. 4). This corresponds well to the value estimated by SDS-PAGE.

FIG. 4 shows elution pattern of nicotianamine synthase from the gel-filtration column. The black circles (●) indicate the enzyme activity and the solid line indicates absorption at 280 nm. The active fraction after hydroxyapatite chromatography was applied to a Sephacryl S300HR (Pharmacia) column (1.5 cm×71 cm, 125 ml), equilibrated with developing buffer (50 mM Tris, 1 mM EDTA, 0.1 M KCl, 0.05% CHAPS, 0.1 mM p-APMSF and 3 mM DTT, pH 8.0). Molecular weight markers used were thyroglobulin (Mr 670,000), γ-globulin (Mr 158,000), ovalbumin (Mr 44,000), and myoglobin (Mr 17,000). The linear flow was 10 cm/hour.

Partial amino acid sequence was determined from purified nicotianamine synthase.

The above explained 30 kDa, 32 kDa and 33 kDa peptides were purified from 1 kg of Fe-deficient barley roots by using a method in example 3 hereinbelow. These were partially degraded using a method in example 4 hereinbelow. Although 32- and 33-kDa peptides could not be completely separated from each other, these might have similar sequence or 32 kDa peptide was presumed to be the degradation product of 33 kDa peptide, and both of them were degraded in together.

The determined partial amino acid sequences indicated that these peptides were very similar in each other (FIG. 5). Further, since the molecular weights of the 33 kDa and 32 kDa (1) fragments had almost unchanged molecular weight as compared with before degradation, this sequence might be N-terminal region of the present enzyme. As a result of computer search of the database, a gene of unknown function having very similar sequence to these sequences was found to exist in *Oryza sativa* and *Alahidopsis thaliana*. Especially, EST-cDNA clones D23792 and D24790 of *Oryza sativa* were very similar with 80.0% identity in a 33-amino acid overlap in the former and 68.4% identity in a 19-amino acid overlap in the latter (FIG. 5).

FIG. 5 shows a comparison with a six partial amino acid sequence determined by nicotianamine synthase originated from barley and similar sequence of graminaceous plants obtained by computer search of the database. Identical amino acid residue is shown in ":". The part of nucleotide sequences indicated by the arrows was applied for the sequences of primer used in PCR.

Cloning and nucleotide sequences of cDNA clones encoding nicotianamine synthase were performed and determined.

PCR amplification of total cDNA prepared from Fe-deficient barley roots using degenerate primers designed from the partial amino acid sequence obtained from the method explained hereinbefore was performed, but the objective DNA could not amplified. Then the primers having single nucleotide sequence (shown by arrows in FIG. 5) from sequences of *Oryza sativa*, D23792 and D24790, were synthesized and PCR amplification was performed. The 205 bp fragment was amplified by PCR using NF and NR primers and the 274 bp fragment was amplified by PCR using IF and IR primers, and these contained the objective sequences. A cDNA library prepared using poly (A)$^+$ RNA from Fe-deficient barley roots was screened and 19 positive clones using the 205 bp fragment probe and 88 positive clones using the 274 fragment bp probe were obtained.

Among the thus obtained clones, the clone designated as HvNAS1, contained a translated region of 985 bp and amino acid sequence deduced therefrom was 328 amino acids residue, with deduced molecular weight of 35,144. This corresponded well with the value estimated by SDS-PAGE and gel-filtration. The partial amino acid sequences of the 32 kDa and 33 kDa peptides were included totally in HvNAS1 (FIG. 6).

FIG. 6 shows full length of HvNAS1 cDNA and amino acid sequence deduced therefrom. The underlined sequences indicate the identical partial amino acid sequences of fragments in the above FIG. 5. Numbers of the nucleotide sequence are indicated to the right of each row. Amino acid numbers are indicated on the left of each row.

The predicted pI of 5.2 matched the value estimated by native isoelectric focusing electrophoresis well. The six clones having very similar sequence other than HvNAS1, i.e. HvNAS2, HvNAS3, HvNAS4, HvNAS5, HvNAS6 and HvNAS7, were also obtained (Table 1, FIG. 7).

FIG. 7 shows comparison of the deduced amino acid sequences of the above 7 cDNA obtained from barley. Asterisks "*" indicates identical amino acid residues in all sequences.

The nucleotide sequences of these clones are shown in SEQ ID NO: 2 (HvNAS1), SEQ ID NO: 4 (HvNAS2), SEQ ID NO: 6 (HvNAS3), SEQ ID NO: 8 (HvNAS4), SEQ ID NO: 10 (HvNAS5), SEQ ID NO: 12 (HvNAS6) and SEQ ID NO: 14 (HvNAS7), respectively. The amino acid sequences of these amino acid sequences are shown in SEQ ID NO: 1 (HvNAS1), SEQ ID NO: 3 (HvNAS2), SEQ ID NO: 5 (HvNAS3), SEQ ID NO: 7 (HvNAS4), SEQ ID NO: 9 (HvNAS5), SEQ ID NO: 11 (HvNAS6) and SEQ ID NO: 13 (HvNAS7), respectively.

TABLE 1

Properties of nas clones

| Clone | Number of Amino Acid Residues | Molecular Weight | pI | Identity to nas 1 (%) | Identity to nas 2 (%) | Identity to nas 4 (%) |
|---|---|---|---|---|---|---|
| HvNAS 1 | 328 | 35144 | 5.20 | — | | |
| HvNAS 2 | 336 | 35839 | 5.07 | 72 | — | |
| HvNAS 3 | 336 | 36013 | 5.47 | 72 | 95 | |
| HvNAS 4 | 330 | 35396 | 4.91 | 73 | 89 | — |
| HvNAS 5 | 283 | 30148 | 5.22 | 61 | 61 | 59 |
| HvNAS 6 | 329 | 35350 | 5.07 | 74 | 89 | 88 |
| HvNAS 7 | 330 | 35244 | 4.98 | 70 | 86 | 91 |

The partial amino acid sequences determined from the 30 kDa peptide were all included in HvNAS5. The 5'- and 3'-non-translated regions of these clones were not similar with each other.

D23792 and D24790 similar to nicotianamine synthase of *Oryzae sativa* were found with about 80% identity to HvNAS1. AC003114 and AB005245 of *Arbidopsis thaliana* were found with about 45% identity to HvNAS1.

The obtained HvNAS1 protein was expressed in *E. coli*.

The PCR amplification of HvNAS1 ORF was cloned with vector pMAL-c2 to express HvNAS1 fused with C-terminal of maltose biding protein. The expression of fused protein is strongly induced by IPTG.

The crude extract was obtained from the transformed *E. coli*, and nicotianamine synthase activity was assayed in the state of the fused protein. The crude extract from the strain transformed with only the vector could not be detected the activity, whereas in case of inserted with HvNAS1 ORF, the activity was detected. Result is shown in FIG. 8.

FIG. 8 shows results of thin layer chromatographic (TLC) analysis of nicotianamine synthase obtained from *E. coli* crude extract expressing a fused protein of maltose binding protein—HvNAS1. In FIG. 8, lane 1: a standard nicotianamine synthase; lane 2: *E. coli* expressing maltose binding protein (SAM); and lane 3: *E. coli* expressing maltose binding protein—HvNAS1 fused protein.

Northern hybridization analysis conducted by the method described in example 7 hereinbelow indicated that this gene was strongly induced in Fe-deficient roots (FIG. 9). This coincides with expression pattern of the present enzyme activity (Higuchi et al. 1994). FIG. 9 shows a result of Northern hybridization analysis using HvNAS1 as a probe. Total RNA was extracted from after one week of Fe-deficient treatment and control barley leaves and roots, and in each lane, 5 μg of RNA were electrophoresed.

Southern hybridization analysis of the barley genome DNA was performed according to the method described in example 8 hereinafter mentioned. Cutting of DNA with BamHI, EcoRI or HindIII produced plurality of fragments, however none of clones obtained at present could be digested by BamHI and EcoRI, consequently nicotianamine synthase gene might exist with multiple copies in genomes of barley and rice (FIG. 10).

FIG. 10 shows Southern—hybridization analysis of HvNAS1 as a probe. Genomic DNAs from barley and rice were digested with BamHI (lanes B), EcoRI (lanes R) and HindIII (lanes H) and 10 μg thereof were electrophoresed in each lane.

Further, using antigen prepared by the method described in example 9 hereinbelow, Western-blot analysis was performed according to the method described in example 10. It was found that the present enzyme protein was rapidly decomposed during the operation in the crude extract prepared for detecting the present enzyme activity (FIG. 11). The staining patterns coincided with the fact that the present enzyme activity was detected on the broad range between 30–35 kDa after SDS-PAGE (refer to FIG. 3).

FIG. 11 shows Western-blot analysis of crude enzyme used for detection of activity. SDS-PAGE was performed using 12.5% acrylamide slab gel. Protein 100 μg was electrophoresed.

The crude extract obtained from denatured protein according to the method described in example 10 hereinbelow was detected as almost single band with 35–36 kDa (FIG. 12). This value coincided with the deduced value from the amino acid sequence.

FIG. 12 shows Western-blot analysis of total protein extracted by trichloroacetic acid/acetone. SDS-PAGE was performed using 12.5% acrylamide slab gel. Protein 100 μg was electrophoresed. Proteins 200 μg extracted from roots and proteins 500 μg extracted from leaves were electrophoresed.

Western-blot analysis after 2-dimention electrophoresis reveals to detect several spots. This coincided with the fact of obtaining plurality of nicotianamine synthase gene. All spots were induced in Fe-deficient roots.

As a result that cDNA library from Fe-deficient rice roots poly (A)+ RNA was screened using probes prepared by cutting HvNAS1 with restriction enzymes ApaLI and XhoI, 20 clones were obtained. These clones were divided into 3 types of clones according to their sequences, and among them, only one type contains ORF full length, which was designated as OsNAS1. Nucleotide sequence of OsNAS1 is shown in SEQ ID NO: 16 and amino acid sequence is shown in SEQ ID NO: 15.

PCR amplification of OsNAS1 ORF was cloned with a vector pMAL-c2 to express a form fused with maltose binding protein C-terminal. The fused protein is strongly induced its expression by IPTG.

Crude extract from the transformed *E. coli* with the fused protein was obtained and nicotianamine synthase activity was assayed in the state of the fused protein. The same activity with HvNAS1 was detected. Result is shown in FIG. 15. FIG. 15 shows results of thin layer chromatographic (TLC) analysis of nicotianamine synthase obtained from *E. coli* crude extract expressing a fused protein of maltose binding protein—OsNAS1. In FIG. 15, lane 1: a standard nicotianamine (NA); lane 2: an extract from *E. coli* expressing maltose binding protein—OsNAS1 fused protein; and lane 3: an extract from *E. coli* expressing maltose binding protein—HvNAS1 fused protein.

Northern hybridization analysis conducted by the method described in example 7 hereinbelow indicated that in contrast to barley, the expression was induced in rice by Fe-deficient treatment not only in roots but also in leaves (FIG. 16). FIG. 16 shows a result of Northern hybridization analysis using OsNAS1 ORF as a probe. Total RNA was extracted from after two weeks of Fe-deficient treatment and control rice leaves and roots, and in each lane, 5 μg of RNA were electrophoresed.

Nucleotide sequence of *Arabidopsis thaliana* similar to HvNAS1 obtained by computer search of the database was used as a primer. PCR amplification for genome DNA of *Arabidopsis thaliana* resulted to obtain three nicotianamine synthase genes. These were designated as AtNAS1, AtNAS2 and AtNAS3.

Nucleotide sequence of these genes are shown in SEQ ID NO: 18 (AtNAS1), SEQ ID NO: 20 (AtNAS2) and SEQ ID NO: 22 (AtNAS3). These amino acid sequences are shown in SEQ ID NO: 17 (AtNAS1), SEQ ID NO: 19 (AtNAS2) and SEQ ID NO: 21 (AtNAS3).

AtNAS1, AtNAS2 and AtNAS3 ORF were amplified with PCR and were cloned with a vector pMAL-c2. Each of them was tried to be expressed in the form of fusing with maltose binding protein C-terminal. The expression of the fused protein was strongly induced by IPTG.

Crude extract from the transformed *E. coli* with the fused protein was obtained and nicotianamine synthase activity was assayed in the state of the fused protein. The activity was detected. Result is shown in FIG. 17. FIG. 17 shows results of TLC analysis of nicotianamine synthase activity obtained from *E. coli* crude extract expressing a fused protein of maltose binding protein—AtNAS. In FIG. 17, lanes 1: a standard nicotianamine (NA) and S-adenosylmethionine; lanes 2: an extract from E. coli expressing only maltose binding protein; lanes 3: an extract from *E. coli* expressing maltose binding protein—AtNAS1 fused protein; lanes 4: an extract from expressing maltose binding protein—AtNAS2 fused protein; and lanes 5: an extract from *E. coli* expressing maltose binding protein—AtNAS3 fused protein.

RT-PCR was conducted according to the method described in example 11 hereinbelow. It was found that AtNAS1 was expressed in the roots and the aboveground parts of *Arabidopsis thaliana*, whereas AtNAS2 was expressed neither in the roots nor in the aboveground parts, and AtNAS3 was expressed only in the roots (FIG. 18). In FIG. 18, lane M shows molecular weight marker. Gene expression was conducted in the aboveground parts, roots and positive controls. In the figure, lanes C: AtNAS1 and AtNAS2 ORF full length were amplified; lanes 1: AtNAS1 specific amplification fragments; lanes 2: AtNAS2 specific amplification fragments; and lanes 3: AtNAS3 specific amplification fragments.

The amount of secreted mugineic acid is reported increased up to 20 mg mugineic acid/g roots dry weight/day (Takagi, 1993). Crude nicotianamine synthase activity detected by the present inventors was sufficient to fulfill it.

Since the present enzyme proteins exist in more than several types and 30 kDa peptide without activity exists, it can be speculated that as a result of aggregation of these peptides, the constructed structure, which is preferable for binding with 3 molecules of S-adenosylmethionine, reveals maximum activity. The molecular weight estimated by gel-filtration was 35,000 (FIG. 4).

Increase in activity by re-aggregation of subunits has not been observed at present. Since the fused protein with maltose binding protein and subunits showed its activity, we have at present an idea that the present enzyme might be a monomer. However, the possibility that large activity can be revealed by constructing multimer, can not completely denied.

The reaction mechanism synthesizing nicotianamine from S-adenosylmethionine may be similar to methyl transfer reaction using S-adenosylmethionine as a methyl donor, and a reaction synthesizing spermidine and spermine from decarboxylated S-adenosylmethionine. The common catalytic domain of these enzymes has been discussed in relation to equivalent amino acids configuration occupying similar positions in higher-order structures (Hashimoto et al. 1998 and Schluckebier et al. 1995).

In future, catalytic domain may be elucidated as the results of comparison with nicotianamine synthase from other plant species or X-ray crystallography.

Induction of nicotianamine synthase activity by Fe-deficiency is a specific phenomenon in graminaceous plants, and is essential for mass production of mugineic acid family. *Oryza sativa* is a plant, in which secretion of mugineic acid family is the least among major graminaceous plants, consequently it is very weak for Fe-deficiency in calcareous soil.

Consequently, as a result of creating transformant *Oryza sativa* having tolerance to Fe-deficiency by introducing nicotianamine synthase gene of the present invention into the graminaceous plants, especially *Oryza sativa*, and expressing large amount at the Fe-deficiency, cultivation of rice in the calcareous soil can be possible.

Heretofore, in the graminaceous plants, nicotianamine has been thought to have only a role as a precursor for synthesis of mugineic acid family. However, since the present invention has elucidated that nicotianamine synthase gene constituted the multiple gene family, it may play other important roles in the graminaceous plants.

In plants, which lack the ability to secrete mugineic acid family, except for graminaceous plants, it has been proposed that nicotianamine plays a key role as an endogenous chelator of divalent metal cations, such as $Fe^{2+}$, $Cu^{2+}$, $Zn^{2+}$ and $Mn^{2+}$, and that it contributes to the homeostasis of those metals (Stephan et al. 1994). Consequently, it may play the same role in the graminaceous plants.

Nicotianamine synthase activity is not induced in dicots, and expression of gene of the present invention may not be induced by Fe-deficiency. We have cloned nicotianamine synthase genes of *Arabidopsis thaliana*. Composition of promoter regions in these genes can elucidate the mechanism of gene expression caused by Fe-deficiency, and the gene of the present invention may play important function not only in the graminaceous plants but also in the dicots.

SEQ ID NO: 1 shows amino acid sequence of nicotianamine synthase of the present invention.

The present invention includes nicotianamine synthase having amino acid sequence shown in SEQ ID NO: 1. However, the present invention is not limited within the above nicotianamine synthase. The nicotianamine synthase of the present invention includes, unless it loses nicotianamine synthase activity, the peptides, in which a part of the amino acid sequence of said peptide is deleted, preferably 50% or less, more preferably 30% or less, or more further preferably 10% or less in the total amino acids, or is substituted by other amino acids, or to which other amino acids are further added, or in which these deletion, substitution and addition may be combined.

Nucleotide sequence coding nicotianamine synthase of the present invention is shown in SEQ ID NO: 2.

The present invention also includes not only a gene coding nicotianamine synthase shown in SEQ ID NO: 2 but also genes coding nicotianamine synthase mentioned hereinabove.

The vector of the present invention introducing the above gene is not specifically limited, and various vectors can be introduced. Preferable vector is the expression vector.

Various cells can be transformed conventionally by using recombinant vector of the present invention. Mass production of nicotianamide can be performed by using the thus obtained transformant. These methods are well known in the person skilled in the art.

Examples of hosts for introducing the gene of the present invention are bacteria, yeasts and cells. Preferable host is plants, especially the graminaceous plant.

Method for introducing gene is not limited. It can be made by using vector or can be directly introduce in genome.

Antibody of the present invention against nicotianamine synthase can be prepared conventionally by using nicotianamine synthase of the present invention. Antibody can be a polyclonal antibody or, if necessary, monoclonal antibody.

Further, a selective breeding of plants, preferably graminaceous plants, can be made by using gene of the present invention. Especially, the gene of the present invention can be applied for improvement of varieties, which can grow even in Fe-deficient soil.

EXAMPLES

The following examples illustrate the present invention, but are not construed as limiting the present invention.

Example 1

Preparation of Plant Material

Seeds of barley (*Hordeum vulgare* L. cv Ehimehadakamugi No. 1) were germinated on wet filter paper and transferred into the standard hydroponic culture solution (Mori and Nishizawa, 1987) in a glass house at natural temperature under natural light. The pH of the hydroponic culture solution was adjusted at 5.5 by 0.5 N HCl everyday. When the third leaves developed, the plants were transferred to the hydroponic culture solution without containing Fe. The pH was maintained at 7.0 by 0.5 N NaOH everyday. The control plants were also cultured in the standard culture solution continuously. The culture solution was renewed once in every week. Two weeks after starting Fe-deficient treatment, when severe iron chlorosis significantly appeared on the 4th and 5th leaves, roots were harvested and frozen in liquid $N_2$ and stored at −80° C. until use.

Example 2

Assay of Nicotianamine Synthase Activity

Modified assay method reported previously by the present inventors (Higuchi et al. 1996a) was used. Enzyme solutions were equilibrated with reaction buffer [50 mM Tris, 1 mM EDTA, 3 mM dithiothreitol (hereinafter designates as DTT), 10 μM (p-amidinophenyl) methanesulfonyl fluoride (hereinafter designates as p-APMSF) and 10 μM trans-epoxysuccinyl-leucylamido-(4-guanidino) butane (hereinafter designates as E-64), pH 8.7]. Buffer exchange was performed by using ultrafiltration unit, Ultrafree C3LGC NMWL10000 (Millipore Co.). S-adenosylmethionine labeled with $^{14}C$ in carboxyl group (Amersham Inc.) was added to the enzyme solution at the final concentration of 20 μM and kept at 25° C. for 15 minutes. The reaction products were separated by thin layer chromatography on silica gel LK6 (Whatman Inc.) using developer (phenol:butanol:formic acid:water=12:3:2:3). Radioactivity of the reaction products was detected by image Analyzer BAS-2000 (Fuji Film Co.). The protein content was assayed by Bradford method using Protein Assay Kit (Bio Rad Inc.).

Example 3

Purification of Nicotianamine Synthase

The following operations were performed at 4° C. and E-64 was added to fractions containing nicotianamine synthase at the final concentration of 10 μM.

The frozen roots were crushed into a fine powder in liquid $N_2$ and homogenized in a household juicer with 200 ml of extraction buffer [0.2 M Tris, 10 mm EDTA, 5% (v/v) glycerol, 10 mM DTT, 0.1 mM E-64, 0.1 mM p-APMSF and 5% (w/v) insoluble polyvinylpyrrolidone (PVP), pH 8.0] per 100 g of roots. The homogenate was centrifuged for 30 minutes at 22,500×g to obtain supernatant. Ammonium sulfate was added to the supernatant to yield a final concentration of 0.4 M and allowed to stand for 1 hour. Again, the mixture was centrifuged for 30 minutes at 22,500×g to obtain supernatant.

The supernatant was loaded onto a TSK gel Butyl Toyopearl 650M column (10 ml bed volume per 100 g of roots), equilibrated with the adsorption buffer [20 mM Tris, 1 mM EDTA, 3 mM DTT, 0.4 M $(NH_4)_2SO_4$ and 0.1 mM p-APMSF, pH 8.0] and eluted with elution buffer [10 mM Tris, 1 mM EDTA, 3 mM DTT, 0.1 mM p-APMSF, 5% glycerol and 0.05% 3-[(3-chloramidopropyl) dimethyl-ammonio] propanesulfonic acid (hereinafter designates as CHAPS), pH 8.0].

KCl was added to the active fraction to give a final concentration of 0.4 M, and 1 M potassium phosphate buffer (pH 8.0) was added to a final concentration of 1 mM of KCl. A hydroxyapatite 100–350 mesh (Nacalai Tesque), equilibrated with the adsorption buffer (1 mM K-P, 10 mM KCl, 3 mM DTT and 0.1 mM p-APMSF, pH 8.0), was prepared at 10 ml per protein 100 mg and the fractions containing nicotianamine synthase were loaded. Nicotianamine synthase was passed through without adsorption. The passed through fraction was loaded onto TSK gel Butyl Toyopearl 650M column (1 ml bed volume per 10 mg of protein), and nicotianamine synthase was eluted in the manner described above.

The active fraction was loaded onto a DEAE-Sepharose FF column (5 ml bed volume per 25 mg of protein, Pharmacia) equilibrated with the adsorption buffer (20 mM Tris, 1 mM EDTA, 3 mM DTT, 0.1 mM p-APMSF and 0.05% CHAPS, pH 8.0) and eluted with stepwise gradient elution of potassium chloride concentration of 0.05 M, 0.1 M, 0.15 M and 0.2 M. Nicotianamine synthase was eluted at 0.15 M of KCl concentration.

The active fraction was loaded onto the Ether Toyopearl 650M column (10 ml bed volume per 100 g of roots), equilibrated with adsorption buffer [20 mM Tris, 1 mM EDTA, 3 mM DTT, 1.2 M $(NH_4)_2SO_4$ and 0.1 mM p-APMSF, pH 8.0]. Nicotianamine synthase was not adsorbed and passed through from the column. The passed through fraction was loaded onto TSK gel Butyl Toyopearl 650M column and fractions containing nicotianamine synthase was eluted. The peptides in the active fraction containing nicotianamine synthase, which was purified by the above column chromatographic treatments, were separated by sodium dodecyl sulfate—polyacrylamide gel electrophoresis (hereinafter designates as SDS-PAGE) using 11% acrylamide slab gels. After SDS-PAGE the gel was stained with 0.3 M copper chloride (Dzandu et al. 1988), and the separated bands were cut out. The gel fragments were destained with 0.25 M EDTA/0.25 M Tris (pH 9.0) and homogenized with the extraction buffer (1% SDS, 25 mM Tris and 192 mM glycine). Each homogenate was electroeluted with SDS-free buffer (25 mM Tris and 192 mM glycine) and peptide was recovered.

Example 4

Determination of Partial Amino Acid Sequence

The isolated nicotianamine synthase was digested chemically with cyanogen bromide (Gross 1967).

After SDS-PAGE treatment, 10-fold volume of 70% (v/v) formic acid and 1% (w/v) cyanogen bromide were added to gel fragments containing nicotianamine synthase and decomposed at 4° C. for overnight. After completion of digestion, the liquid part was collected and dried in vacuo. The dried substance was dissolved in SDS-PAGE sample buffer, and allowed to stand at room temperature for overnight, then the digested product was separated by SDS-PAGE using 16.5% acrylamide gel containing Tricine (Schagger and Jagow, 1987). The peptides were transferred onto a PVDF membrane by electroblotting (Towbin et al. 1979) and stained with amido black. The stained bands were cut out and the amino acid sequence was determined from N-terminal side of each peptide by Edman degradation in gas-phase sequencer (model 492A protein sequencer, Applied Biosystems Inc.).

Example 5

Cloning of Nicotianamine Synthase Genes

PCR amplification was conducted for cDNA originated from Fe-deficient barley roots using primers, which were synthesized based on the obtained partial amino acid sequence. A pYH23 cDNA library prepared from the poly $(A)^+RNA$ of Fe-deficient barley roots was screened with the thus obtained DNA fragments of PCR product, which was labeled with $[\alpha-^{32}P]dATP$ using the random primer kit (Takara Shuzo Co.), as the primers. The isolated cDNA clones were sequenced by cycle sequencing kit (Shimadzu Bunko Co.) using Shimadzu DNA sequencer DSQ-2000L.

PCR amplification was conducted for genomic DNA of *Arabidopsis thaliana* using primers, which were synthesized based on nucleotide sequences of AC003114 and AB005245 of *Arabidopsis thaliana*. The thus obtained DNA fragments were sequenced by cycle sequencing kit (Shimadzu Bunko Co.) using Shimadzu DNA sequencer DSQ-1000L.

The determined nucleotide sequence is shown in SEQ ID NO: 2.

Example 6

Expression of NAS1 Protein in E. coli

A fragment, in which EcoRI site was introduced into the upstream of the first ATG of the HvNAS1 cDNA and PstI and BamHI sites were introduced into the downstream of the stop codon of the HvNAS1 cDNA, was amplified by PCR. The thus obtained amplified product was subcloned in the pBluescriptII SK– using EcoRI site and BamHI site, and the correct nucleotide sequence was confirmed. The fragment between EcoRI site and PstI site was cloned into pMAL-c2 to make expression in the form of fusing the HvNAS1 to the C-terminal of maltose binding protein.

A fragment, in which EcoRI site was introduced into the upstream of the first ATG of the OsNAS1 and HindIII site was introduced into the downstream of the stop codon of the OsNAS1, was amplified by PCR. The thus obtained amplified product was subcloned in the pBluescriptII SK– using EcoRI site and HindIII site, and the correct nucleotide sequence was confirmed. The fragment between EcoRI site and HindIII site was cloned into pMAL-c2 to make expression in the form of fusing the OsNAS1 to the C-terminal of maltose binding protein.

A fragment, in which EcoRI site was introduced into the upstream of the first ATG of the AtNAS1, AtNAS2 and AtNAS3 and XbaI site was introduced into the downstream of the stop codon of the AtNAS1, AtNAS2 and AtNAS3, was amplified by PCR. The thus obtained amplified products were subcloned in the pBluescriptII SK–, and the correct nucleotide sequences were confirmed. The fragment between EcoRI site and XbaI site was cloned into pMAL-c2 to make expression in the form of fusing the AtNAS1, AtNAS2 and AtNAS3 to the C-terminal of maltose binding proteins, respectively.

E. coli strain XL1-Blue was used as a host for expressing the said fused protein. pMAL-c2-HvNAS1 and pMAL-c2, respectively, were introduced into YL1-Blue. The thus obtained recombinant bacteria were cultured in LB medium containing ampicillin and tetracycline, each 50 µg/ml, at 37° C. until the OD 600 of the culture reached 0.5. Isopropyl β-D-thiogalactopyranaoside (IPTG) was added to the final concentration of 0.3 mM, and continuously cultured at 37° C. for 3 hours, and collected bacterial cells. Cells were suspended in 10 mM Tris buffer containing 0.2 M NaCl, 1 mM EDTA, 3 mM DTT and 0.1 mM E-64, pH 7.4 and frozen with liquid nitrogen. This was melted in ice water and ultrasonication for 15 seconds was repeated for 10 times. Nicotianamine synthase activity of the thus obtained crude extract was assayed according to the method described in example 2 and the enzyme activity was confirmed.

Example 7

Northern Hybridization

Northern hybridization of barley RNA was performed using DNA fragment, which was prepared by cutting HvNAS1 cDNA with HindIII and NotI and labeled with [α-$^{32}$P]dATP, as a probe. Total RNA was extracted from barley (Naito et al. 1988). The extracted RNA was separated by 1.4% agarose gel electrophoresis, and blotted onto Hybond-N$^+$ membranes (Amersham). Northern hybridization of rice RNA was performed using OsNAS1 ORF, which was labeled with [α-$^{32}$P]dATP, as a probe. Total RNA was extracted from rice. The extracted RNA was separated by 1.4% agarose gel electrophoresis, and blotted onto Hybond-N$^+$ membranes (Amersham). The membrane was hybridized with the probe in 0.5 M Church phosphate buffer (Church and Gilbert 1984), 1 mM EDTA, 7% (w/v) SDS with 100 µg/ml salmon sperm DNA at 65° C. for overnight. The membrane was washed with buffer containing 40 mM Church phosphate buffer and 1% (w/v) SDS at 65° C. for 10 minutes. After the washing was repeated once again, the membrane was washed with buffer containing 0.2×SSPE and 0.1% (w/v) SDS at 65° C. for 10 minutes. Radioactivity was detected using the image analyzer BAS-2000.

Results are shown in FIG. 9 and FIG. 16.

Example 8

Southern Hybridization

Genomic DNA was extracted from leaves of barley and rice. The extract was digested with BamHI, EcoRI or HindIII, separated on a 0.8% (w/v) agarose gel electrophoresis, and transferred onto Hybond-N$^+$ membranes (Amersham). The hybridization was performed according to the method described in example 7 and radioactivity was detected.

Result is shown in FIG. 10.

Example 9

Preparation of Polyclonal Antibody

Two rats were immunized using the antigen containing about 100 µg of isolated nicotianamine synthase. The antigen was the same sample as that determined the partial amino acid sequence. The complete Freund's adjuvant was used at the first immunization and the incomplete Freund's adjuvant was used since the second immunization. All the constituents of the blood were corrected after the rats were immunized four times, and the obtained serum was preserved at –80° C.

Example 10

Western Blotting Analysis

Total protein was extracted using trichloroacetic acid and acetone (Damerval et al. 1986). The plants were crashed in the liquid nitrogen until powder was obtained, and mixed with acetone containing 0.1% (v/v) 2-mercaptoethanol. The protein was precipitated by allowing to stand at –20° C. for 1 hour, and the precipitate was collected by centrifugation at 16,000×g for 30 minutes. The precipitate was suspended in acetone containing 0.1% (v/v) 2-mercaptoethanol and allowed to stand at –20° C. for 1 hour, then collected the precipitate by centrifugation at 16,000×g for 30 minutes. The precipitate was dried in vacuo, and dissolved in the sample buffer [9.5 M urea, 2% (w/v) Triton X-100 and 5% (v/v) 2-ME], then centrifuged at 16,000×g for 10 minutes to obtain the supernatant. The proteins contained in the supernatant were separated by SDS-PAGE or the denaturing two-dimensional electrophoresis (O'Farrell 1975) and transferred onto PVDF membrane. Western blotting analysis was performed by applying the primary antibody containing anti-nicotianamine synthase antibody prepared in example 9 and the secondary antibody containing horse radish binding anti-mouse IgG (H+L) goat antibody (Wako Pure Chemicals Co.) on the membrane and coloring with diaminobenzidin.

Result is shown in FIG. 12. SDS-PAGE was performed using 12.5% acrylamide slab gel. Protein 100 μg was electrophoresed. Proteins of roots 200 μg and leaves 500 μg were electrophoresed.

Example 11

RT-PCR

Total RNA was extracted from *Arabidopsis thaliana*. RT-PCR was performed with 1 μg RNA as a template by using the EZ rTth RNA PCR kit (Parkin Elmer Inc.). Specific primers for AtNAS1, AtNAS2 and AtNAS3, respectively, were used.

Result is shown in FIG. 18.

INDUSTRIAL APPLICABILITY

Various cells are transformed according to the conventional method by using recombinant vectors of the present invention. Mass production of nicotianamine can be performed by using the obtained transformant. These methods can be performed according to the method known in the person skilled in the art.

Selective breeding of plants, preferably graminaceous plants can also be performed using genes of the present invention. Especially, genes of the present invention can be applied for improving varieties, which can grow on Fe-deficient soil.

---

The invention claimed is:

1. An isolated or purified enzyme exhibiting nicotianamine synthase activity, wherein the enzyme comprises a polypeptide that is at least 90% identical to SEQ ID NO:1.

2. The isolated or purified enzyme of claim 1, wherein the enzyme comprises the polypeptide having the amino acid sequence of SEQ ID NO: 1.

3. The enzyme according to claim 1, wherein the enzyme comprises the consensus amino acid sequence of $_{199}$DVVFLAALVGM$_{209}$ (SEQ ID NO: 27).

4. The enzyme of claim 1, wherein the polypeptide further comprises all of the conserved amino acid residues of SEQ ID NO: 1 that is:

L(11), K(14), I(15), I(22), L(25), L(28), P(30), L(37), F(38), L(41), V(42), C(45), P(47), D(52), V(53), Q(61), M(63), R(64), L(67), I(68), C(71), A(74), E(75), L(78), E(79), H(81), L(86), D(90), P(92), L(93), H(95), L(96), F(99), P(100), Y(101), N(104), Y(105), L(108), L(111), E(112), L(115), L(116), A(129), F(130), G(132), S(133), G(134), P(135), L(136), P(137), S(140), L(143), A(144), H(147), L(148), F(153), N(155), A(162), N(163), A(166), L(169), R(180), M(181), F(183), T(185), L(195), D(199), V(200), V(201), F(202), L(203), A(204), A(205), V(207), G(208), M(209), K(214), H(220), L(221), H(224), M(225), G(228), A(229), L(231), R(239), F(241), L(242), Y(243), P(244), V(246), G(255), F(256), V(258), L(259), V(261), H(263), P(264), V(268), N(270), S(271), K(277) (SEQ ID NO:29).

5. The enzyme of claim 1, wherein the polypeptide has more than 95% identity with the amino acid sequence of SEQ ID NO: 1.

6. The enzyme of claim 1, wherein the nicotianamine synthase activity is measured in an assay in a comparison with the enzyme of SEQ ID NO:1.

7. The enzyme of claim 1, wherein the enzyme is isolated or purified from barley.

8. A mutated enzyme exhibiting nicotianamine synthase activity, wherein the enzyme:
a. is a polypeptide having more than 95% identity with the amino acid sequence of SEQ ID NO: 1, comprising at least one consensus sequence of SEQ ID NO: 1 that is:
(1) $_{25}$LPXLSPSPXVDRLFTXLVXACVPXSPVD-VTKL$_{56}$ (SEQ ID NO: 23)
(2) $_{67}$LIRLCSXAEGXLEAHY$_{82}$ (SEQ ID NO: 24)
(3) $_{92}$PLDHLGXFPY$_{101}$ (SEQ ID NO: 25)
(4) $_{128}$VAFXGSGPLPFSS$_{140}$ (SEQ ID NO: 26)
(5) $_{199}$DVVFLAALVGM$_{209}$ (SEQ ID NO: 27)
(6) $_{253}$RGGFXVLAVXHP$_{264}$ (SEQ ID NO: 28); and
b. has more than 25% of the relative nicotianamine synthase activity of the enzyme of SEQ ID NO: 1.

9. The enzyme of claim 8, wherein the polypeptide further comprises all of the conserved amino acid residues of SEQ ID NO: 1 that is:

L(11), K(14), I(15), I(22), L(25), L(28), P(30), L(37), F(38), L(41), V(42), C(45), P(47), D(52), V(53), Q(61), M(63), R(64), L(67), I(68), C(71), A(74), E(75), L(78), E(79), H(81), L(86), D(90), P(92), L(93), H(95), L(96), F(99), P(100), Y(101), N(104), Y(105), L(108), L(111), E(112), L(115), L(116), A(129), F(130), G(132), S(133), G(134), P(135), L(136), P(137), S(140), L(143), A(144), H(147), L(148), F(153), N(155), A(162), N(163), A(166), L(169), R(180), M(181), F(183), T(185), L(195), D(199), V(200), V(201), F(202), L(203), A(204), A(205), V(207), G(208), M(209), K(214), H(220), L(221), H(224), M(225), G(228), A(229), L(231), R(239), F(241), L(242), Y(243), P(244), V(246), G(255), F(256), V(258), L(259), V(261), H(263), P(264), V(268), N(270), S(271), K(277) (SEQ ID NO: 29).

10. The enzyme of claim 8, wherein the nicotianamine synthase activity is measured in an assay in a comparison with the enzyme of SEQ ID NO:1.

11. The enzyme of claim 8, wherein the polypeptide has more than 97% identity with the amino acid sequence of SEQ ID NO: 1.

12. The enzyme of claim 1, wherein the polypeptide has more than 97% identity with the amino acid sequence of SEQ ID NO: 1.

13. An isolated, purified, or mutated enzyme exhibiting nicotianamine synthase activity, wherein the enzyme comprises an active fragment of the amino acid sequence of SEQ ID NO: 1, the active fragment comprising a polypeptide, wherein the polypeptide:
a. comprises at least one consensus sequence of SEQ ID NO: 1 that is:
(1) $_{25}$LPXLSPSPXVDRLFTXLVXACVPXSPVD-VTKL$_{56}$ (SEQ ID NO: 23)
(2) $_{67}$LIRLCSXAEGXLEAHY$_{82}$ (SEQ ID NO: 24)
(3) $_{92}$PLDHLGXFPY$_{101}$ (SEQ ID NO: 25)
(4) $_{128}$VAFXGSGPLPFSS$_{140}$ (SEQ ID NO: 26)
(5) $_{199}$DVVFLAALVGM$_{209}$ (SEQ ID NO: 27)
(6) $_{253}$RGGFXVLAVXHP$_{264}$ (SEQ ID NO: 28); and
b. has more than 25% of the relative nicotianamine synthase activity of the enzyme of SEQ ID NO:1.

14. An isolated or purified barley enzyme exhibiting nicotianamine synthase activity, wherein:
a. the enzyme is:
i. isolated or purified from barley; or
ii. expressed directly or indirectly from a nucleic acid isolated or purified from barley; or
iii. expressed directly or indirectly from a chimeric nucleic acid at least partially isolated or purified from barley;
b. the enzyme comprises a polypeptide having at least 90% identity with the amino acid sequence of SEQ ID NO: 1, comprising at least one consensus sequence of SEQ ID NO: 1 that is:
(1) $_{25}$LPXLSPSPXVDRLFTXLVXACVPXSPVD-VTKL$_{56}$ (SEQ ID NO: 23)
(2) $_{67}$LIRLCSXAEGXLEAHY$_{82}$ (SEQ ID NO: 24)
(3) $_{92}$PLDHLGXFPY$_{101}$ (SEQ ID NO: 25)
(4) $_{128}$VAFXGSGPLPFSS$_{140}$ (SEQ ID NO: 26)
(5) $_{199}$DVVFLAALVGM$_{209}$ (SEQ ID NO: 27)
(6) $_{253}$RGGFXVLAVXHP$_{264}$ (SEQ ID NO: 28); and
c. the enzyme has more than 25% of the relative nicotianamine synthase activity of the enzyme of SEQ ID NO: 1.

15. The enzyme of claim 14, wherein the polypeptide further comprises all of the conserved amino acid residues of SEQ ID NO: 1 that is:

L(11), K(14), I(15), I(22), L(25), L(28), P(30), L(37), F(38), L(41), V(42), C(45), P(47), D(52), V(53), Q(61), M(63), R(64), L(67), I(68), C(71), A(74), E(75), L(78), E(79), H(81), L(86), D(90), P(92), L(93), H(95), L(96), F(99), P(100), Y(101), N(104), Y(105), L(108), L(111), E(112), L(115), L(116), A(129), F(130), G(132), S(133), G(134), P(135), L(136), P(137), S(140), L(143), A(144), H(147), L(148), F(153), N(155), A(162), N(163), A(166), L(169), R(180), M(181), F(183), T(185), L(195), D(199), V(200), V(201), F(202), L(203), A(204), A(205), V(207), G(208), M(209), K(214), H(220), L(221), H(224), M(225), G(228), A(229), L(231), R(239), F(241), L(242),

Y(243), P(244), V(246), G(255), F(256), V(258), L(259), V(261), H(263), P(264), V(268), N(270), S(271), K(277) (SEQ ID NO: 29).

16. The enzyme of claim 14, wherein the polypeptide has more than 90% identity with the amino acid sequence of SEQ ID NO: 1.

17. The enzyme of claim 14, wherein the polypeptide has more than 95% identity with the amino acid sequence of SEQ ID NO: 1.

18. The enzyme of claim 14, wherein the nicotianamine synthase activity is measured in an assay in a comparison with the enzyme of SEQ ID NO:1.

19. An isolated or purified enzyme exhibiting nicotianamine synthase activity, wherein the enzyme consists of the polypeptide set forth as SEQ ID NO: 1.

20. The isolated or purified enzyme of claim 1, comprising at least one consensus sequence of SEQ ID NO: 1 selected from the group consisting of:

(1) $_{25}$LPXLSPSPXVDRLFTXLVXACVPXSPVDVTKL$_{56}$ (SEQ ID NO: 23)
(2) $_{67}$LIRLCSXAEGXLEAHY$_{82}$ (SEQ ID NO: 24)
(3) $_{92}$PLDHLGXFPY$_{101}$ (SEQ ID NO: 25)
(4) $_{128}$VAFXGSGPLPFSS$_{140}$ (SEQ ID NO: 26)
(5) $_{199}$DVVFLAALVGM$_{209}$ (SEQ ID NO: 27)
(6) $_{253}$RGGFXVLAVXHP$_{264}$ (SEQ ID NO: 28); and b. has more than 25% of the relative nicotianamine synthase activity of the enzyme of SEQ ID NO:1.

* * * * *

SEQUENCE LISTING

```
<160> NUMBER OF SEQ ID NOS: 37

<210> SEQ ID NO 1
<211> LENGTH: 328
<212> TYPE: PRT
<213> ORGANISM: Hordeum vulgare

<400> SEQUENCE: 1

Met Asp Ala Gln Asn Lys Glu Val Ala Ala Leu Ile Glu Lys Ile Ala
 1               5                  10                  15

Gly Ile Gln Ala Ala Ile Ala Glu Leu Pro Ser Leu Ser Pro Ser Pro
            20                  25                  30

Glu Val Asp Arg Leu Phe Thr Asp Leu Val Thr Ala Cys Val Pro Pro
        35                  40                  45

Ser Pro Val Asp Val Thr Lys Leu Ser Pro Glu His Gln Arg Met Arg
    50                  55                  60

Glu Ala Leu Ile Arg Leu Cys Ser Ala Ala Glu Gly Lys Leu Glu Ala
65                  70                  75                  80

His Tyr Ala Asp Leu Leu Ala Thr Phe Asp Asn Pro Leu Asp His Leu
                85                  90                  95

Gly Leu Phe Pro Tyr Tyr Ser Asn Tyr Val Asn Leu Ser Arg Leu Glu
            100                 105                 110

Tyr Glu Leu Leu Ala Arg His Val Pro Gly Ile Ala Pro Ala Arg Val
        115                 120                 125

Ala Phe Val Gly Ser Gly Pro Leu Pro Phe Ser Ser Leu Val Leu Ala
    130                 135                 140

Ala His His Leu Pro Glu Thr Gln Phe Asp Asn Tyr Asp Leu Cys Gly
145                 150                 155                 160

Ala Ala Asn Glu Arg Ala Arg Lys Leu Phe Gly Ala Thr Ala Asp Gly
                165                 170                 175

Val Gly Ala Arg Met Ser Phe His Thr Ala Asp Val Ala Asp Leu Thr
            180                 185                 190

Gln Glu Leu Gly Ala Tyr Asp Val Val Phe Leu Ala Ala Leu Val Gly
        195                 200                 205

Met Ala Ala Glu Glu Lys Ala Lys Val Ile Ala His Leu Gly Ala His
    210                 215                 220

Met Val Glu Gly Ala Ser Leu Val Val Arg Ser Ala Arg Pro Arg Gly
225                 230                 235                 240

Phe Leu Tyr Pro Ile Val Asp Pro Glu Asp Ile Arg Arg Gly Gly Phe
                245                 250                 255
```

```
Glu Val Leu Ala Val His His Pro Glu Gly Glu Val Ile Asn Ser Val
            260                 265                 270

Ile Val Ala Arg Lys Ala Val Glu Ala Gln Leu Ser Gly Pro Gln Asn
        275                 280                 285

Gly Asp Ala His Ala Arg Gly Ala Val Pro Leu Val Ser Pro Pro Cys
    290                 295                 300

Asn Phe Ser Thr Lys Met Glu Ala Ser Ala Leu Glu Lys Ser Glu Glu
305                 310                 315                 320

Leu Thr Ala Lys Glu Leu Ala Phe
                325

<210> SEQ ID NO 2
<211> LENGTH: 1295
<212> TYPE: DNA
<213> ORGANISM: Hordeum vulgare
<220> FEATURE:
<221> NAME/KEY: CDS
<222> LOCATION: (55)..(1041)

<400> SEQUENCE: 2
```

| | | |
|---|---|---|
| gcgttcagag gcttccagag ttcttccggt caccaagaag catttgatca taac atg<br>                                                                                                   Met<br>                                                                                                   1 | | 57 |

```
gat gcc cag aac aag gag gtc gct gct ctg atc gag aag atc gcc ggt      105
Asp Ala Gln Asn Lys Glu Val Ala Ala Leu Ile Glu Lys Ile Ala Gly
            5                  10                  15 atc cag gcc gcc atc gcc gag ctg ccg tcg ctg agc ccg tcc ccc gag      153
Ile Gln Ala Ala Ile Ala Glu Leu Pro Ser Leu Ser Pro Ser Pro Glu
        20                  25                  30 gtc gac agg ctc ttc acc gac ctc gtc acg gcc tgc gtc ccg ccg agc      201
Val Asp Arg Leu Phe Thr Asp Leu Val Thr Ala Cys Val Pro Pro Ser
    35                  40                  45 ccc gtc gac gtg acg aag ctc agc ccg gag cac cag agg atg cgg gag      249
Pro Val Asp Val Thr Lys Leu Ser Pro Glu His Gln Arg Met Arg Glu
50                  55                  60                  65 gct ctc atc cgc ttg tgc tcc gcc gcc gag ggg aag ctc gag gcg cac      297
Ala Leu Ile Arg Leu Cys Ser Ala Ala Glu Gly Lys Leu Glu Ala His
                70                  75                  80 tac gcc gac ctg ctc gcc acc ttc gac aac ccg ctc gac cac ctc ggc      345
Tyr Ala Asp Leu Leu Ala Thr Phe Asp Asn Pro Leu Asp His Leu Gly
            85                  90                  95 ctc ttc ccg tac tac agc aac tac gtc aac ctc agc agg ctg gag tac      393
Leu Phe Pro Tyr Tyr Ser Asn Tyr Val Asn Leu Ser Arg Leu Glu Tyr
        100                 105                 110 gag ctc ctg gcg cgc cac gtg ccg ggc atc gcg ccg gcg cgc gtc gcc      441
Glu Leu Leu Ala Arg His Val Pro Gly Ile Ala Pro Ala Arg Val Ala
    115                 120                 125 ttc gtc ggc tcc ggc ccg ctg ccg ttc agc tcg ctc gtc ctc gcc gcg      489
Phe Val Gly Ser Gly Pro Leu Pro Phe Ser Ser Leu Val Leu Ala Ala
130                 135                 140                 145 cac cac ctg ccc gag acc cag ttc gac aac tac gac ctg tgc ggc gcg      537
His His Leu Pro Glu Thr Gln Phe Asp Asn Tyr Asp Leu Cys Gly Ala
                150                 155                 160 gcc aac gag cgc gcc agg aag ctg ttc ggc gcg acg gcg gac ggc gtc      585
Ala Asn Glu Arg Ala Arg Lys Leu Phe Gly Ala Thr Ala Asp Gly Val
            165                 170                 175 ggc gcg cgt atg tcg ttc cac acg gcg gac gtc gcc gac ctc acc cag      633
Gly Ala Arg Met Ser Phe His Thr Ala Asp Val Ala Asp Leu Thr Gln
        180                 185                 190
```

-continued

```
gag ctc ggc gcc tac gac gtg gtc ttc ctc gcc gcg ctc gtc ggc atg         681
Glu Leu Gly Ala Tyr Asp Val Val Phe Leu Ala Ala Leu Val Gly Met
    195                 200                 205 gca gcc gag gag aag gcc aag gtg att gcc cac ctg ggc gcg cac atg         729
Ala Ala Glu Glu Lys Ala Lys Val Ile Ala His Leu Gly Ala His Met
210                 215                 220                 225 gtg gag ggg gcg tcc ctg gtc gtg cgg agc gca cgg ccc cgc ggc ttt         777
Val Glu Gly Ala Ser Leu Val Val Arg Ser Ala Arg Pro Arg Gly Phe
                230                 235                 240 ctt tac ccc att gtc gac ccg gag gac atc agg cgg ggt ggg ttc gag         825
Leu Tyr Pro Ile Val Asp Pro Glu Asp Ile Arg Arg Gly Gly Phe Glu
                245                 250                 255 gtg ctg gcc gtg cac cac ccg gaa ggt gag gtg atc aac tct gtc atc         873
Val Leu Ala Val His His Pro Glu Gly Glu Val Ile Asn Ser Val Ile
        260                 265                 270 gtc gcc cgt aag gcc gtc gaa gcg cag ctc agt ggg ccg cag aac gga         921
Val Ala Arg Lys Ala Val Glu Ala Gln Leu Ser Gly Pro Gln Asn Gly
    275                 280                 285 gac gcg cac gca cgg ggc gcg gtg ccg ttg gtc agc ccg cca tgc aac         969
Asp Ala His Ala Arg Gly Ala Val Pro Leu Val Ser Pro Pro Cys Asn
290                 295                 300                 305 ttc tcc acc aag atg gag gcg agc gcg ctt gag aag agc gag gag ctg        1017
Phe Ser Thr Lys Met Glu Ala Ser Ala Leu Glu Lys Ser Glu Glu Leu
                310                 315                 320 acc gcc aaa gag ctg gcc ttt tga ttgaagagtg cgcgtggtca ttctgtcgcc       1071
Thr Ala Lys Glu Leu Ala Phe
                325 tgcgatcgtg gtaactttcc tactcgtgtg tgttttgatg tttgtgcctg taagagttat     1131 gcttccggcc ttgtgctgtt aatttacacg cgttacatgt agtacttgta tttatacctg     1191 gaataacggt atgtaacata aatattagtg ggatttgaag tgtaatgcta ataataaga      1251 aaacttgatg cagacattca aaaaaaaaaa aaaaaaaaaa aaaa                      1295

<210> SEQ ID NO 3
<211> LENGTH: 335
<212> TYPE: PRT
<213> ORGANISM: Hordeum vulgare

<400> SEQUENCE: 3

Met Ala Ala Gln Asn Asn Gln Glu Val Asp Ala Leu Val Glu Lys Ile
1               5                   10                  15

Thr Gly Leu His Ala Ala Ile Ala Lys Leu Pro Ser Leu Ser Pro Ser
            20                  25                  30

Pro Asp Val Asp Ala Leu Phe Thr Glu Leu Val Thr Ala Cys Val Pro
        35                  40                  45

Pro Ser Pro Val Asp Val Thr Lys Leu Gly Pro Glu Ala Gln Glu Met
    50                  55                  60

Arg Glu Gly Leu Ile Arg Leu Cys Ser Glu Ala Glu Gly Lys Leu Glu
65                  70                  75                  80

Ala His Tyr Ser Asp Met Leu Ala Ala Phe Asp Lys Pro Leu Asp His
                85                  90                  95

Leu Gly Met Phe Pro Tyr Tyr Asn Asn Tyr Ile Asn Leu Ser Lys Leu
            100                 105                 110

Glu Tyr Glu Leu Leu Ala Arg Tyr Val Pro Gly Gly Tyr Arg Pro Ala
        115                 120                 125

Arg Val Ala Phe Ile Gly Ser Gly Pro Leu Pro Phe Ser Ser Phe Val
    130                 135                 140
```

-continued

| | | | | | | | | | | | | | | |
|---|---|---|---|---|---|---|---|---|---|---|---|---|---|---|
| Leu | Ala | Ala | Arg | His | Leu | Pro | Asp | Thr | Met | Phe | Asp | Asn | Tyr | Asp | Leu |
| 145 | | | | 150 | | | | | 155 | | | | | 160 | |
| Cys | Gly | Ala | Ala | Asn | Asp | Arg | Ala | Ser | Lys | Leu | Phe | Arg | Ala | Asp | Arg |
| | | | | 165 | | | | | 170 | | | | | 175 | |
| Asp | Val | Gly | Ala | Arg | Met | Ser | Phe | His | Thr | Ala | Asp | Val | Ala | Asp | Leu |
| | | 180 | | | | | | 185 | | | | | 190 | | |
| Ala | Gly | Glu | Leu | Ala | Lys | Tyr | Asp | Val | Val | Phe | Leu | Ala | Ala | Leu | Val |
| | | 195 | | | | | 200 | | | | | 205 | | | |
| Gly | Met | Ala | Ala | Glu | Asp | Lys | Ala | Lys | Val | Ile | Ala | His | Leu | Gly | Ala |
| | 210 | | | | | 215 | | | | | 220 | | | | |
| His | Met | Ala | Asp | Gly | Ala | Ala | Leu | Val | Val | Arg | Ser | Ala | His | Gly | Ala |
| 225 | | | | | 230 | | | | | 235 | | | | | 240 |
| Arg | Gly | Phe | Leu | Tyr | Pro | Ile | Val | Asp | Pro | Gln | Asp | Ile | Gly | Arg | Gly |
| | | | | 245 | | | | | 250 | | | | | 255 | |
| Gly | Phe | Glu | Val | Leu | Ala | Val | Cys | His | Pro | Asp | Asp | Val | Val | Asn | |
| | | | 260 | | | | | 265 | | | | | 270 | | |
| Ser | Val | Ile | Ile | Ala | Gln | Lys | Ser | Lys | Asp | Val | His | Ala | Asp | Gly | Leu |
| | | 275 | | | | | 280 | | | | | 285 | | | |
| Gly | Ser | Gly | Arg | Gly | Ala | Gly | Gly | Gln | Tyr | Ala | Arg | Gly | Thr | Val | Pro |
| | 290 | | | | | 295 | | | | | 300 | | | | |
| Val | Val | Ser | Pro | Pro | Cys | Arg | Phe | Gly | Glu | Met | Val | Ala | Asp | Val | Thr |
| 305 | | | | | 310 | | | | | 315 | | | | | 320 |
| Gln | Asn | His | Lys | Arg | Asp | Glu | Phe | Ala | Asn | Ala | Glu | Val | Ala | Phe | |
| | | | | 325 | | | | | 330 | | | | | 335 | |

<210> SEQ ID NO 4
<211> LENGTH: 1342
<212> TYPE: DNA
<213> ORGANISM: Hordeum vulgare

<400> SEQUENCE: 4

```
ctcctgtgcc tgtcctgagg taccaagaac accagtgaaa tggctgccca gaacaaccag      60
gaggtggatg ccctggtgga gaagatcacc gggctccatg ccgcaatcgc caagctgccg     120
tcgctcagcc catccccgga cgtcgacgcg ctcttcacgg agctggtcac ggcgtgcgtt     180
ccaccgagtc cagtggacgt gaccaagctc gggccggagg cgcaggagat gcggagggc      240
ctcatccgcc tatgctccga ggccgagggg aagctggagg cgcactactc cgacatgctc     300
gccgccttcg acaagccgct ggatcacctc ggcatgttcc cctactacaa caactacatc     360
aacctcagca agctcgagta cgagctcctg cccgctacg tgcctggcgg ctatcgcccg     420
gcgcgcgtcg cgttcatcgg ctccggcccg ctgccgttca gctcctttgt cctggccgcg    480
cgccacctgc ccgacaccat gttcgacaac tatgacctgt gcggtgcggc caacgatcgc    540
gccagcaagc tcttccgcgc ggatcgcgac gtgggtgccc gcatgtcgtt ccacacggcc    600
gacgtcgcgg acctcgccgg cgagctcgcc aagtacgacg ttgtcttcct ggccgcactc    660
gtcggcatgg ccgccgagga caaggcgaag gtgatcgcgc acctcggcgc acacatggca    720
gacgggcgg ccctcgtcgt gcgcagcgca cggagcgc gcgggttcct gtacccgatc       780
gtcgacccc aggacatcgg ccgaggcggg ttcgaggtgc tggccgtgtg ccatcccgac     840
gacgacgtgg tgaactccgt catcatcgca cagaagtcca aggacgtgca tgccgatgga    900
cttggcagcg gcgtggtgc cggtggacag tacgcgcggg gcacggtgcc tgttgtcagc    960
cccccgtgca ggttcggcga gatggtggcg gacgtgaccc agaaccacaa gagagacgag   1020
tttgccaacg ccgaagtggc cttttgatcg ttcgctgcga gggtgtgcat ccatgatcca   1080
```

```
tccatacctc gttctgtgat tgcatcaagc ttgcaatcgt atgcatttca agtcacgtgt    1140
tgcttctatc caataatgta cgtgtggtgt ttacacgcga atgtcttgta gacctttgta    1200
tgtgtacaag tgaattttaa ttcacaagta catataatgg tcaccattga aaagatgttt    1260
agtgtgtgtt ttccaatata tgtttgtgta aggttcatca tctaataaaa tatgtttgga    1320
acccaaaaaa aaaaaaaaaa aa                                              1342

<210> SEQ ID NO 5
<211> LENGTH: 335
<212> TYPE: PRT
<213> ORGANISM: Hordeum vulgare

<400> SEQUENCE: 5

Met Ala Ala Gln Asn Asn Asn Lys Asp Val Ala Ala Leu Val Glu Lys
  1               5                  10                  15

Ile Thr Gly Leu His Ala Ala Ile Ala Lys Leu Pro Ser Leu Ser Pro
             20                  25                  30

Ser Pro Asp Val Asp Ala Leu Phe Thr Glu Leu Val Thr Ala Cys Val
         35                  40                  45

Pro Pro Ser Pro Val Asp Val Thr Lys Leu Gly Pro Glu Ala Gln Glu
     50                  55                  60

Met Arg Glu Gly Leu Ile Arg Leu Cys Ser Ala Glu Gly Lys Leu
 65                  70                  75                  80

Glu Ala His Tyr Ser Asp Met Leu Ala Ala Phe Asp Asn Pro Leu Asp
                 85                  90                  95

His Leu Gly Ile Phe Pro Tyr Tyr Ser Asn Tyr Ile Asn Leu Ser Lys
            100                 105                 110

Leu Glu Tyr Glu Leu Leu Ala Arg Tyr Val Arg Arg His Arg Pro Ala
        115                 120                 125

Arg Val Ala Phe Ile Gly Ser Gly Pro Leu Pro Phe Ser Ser Phe Val
    130                 135                 140

Leu Ala Ala Arg His Leu Pro Asp Thr Met Phe Asp Asn Tyr Asp Leu
145                 150                 155                 160

Cys Gly Ala Ala Asn Asp Arg Ala Ser Lys Leu Phe Arg Ala Asp Thr
                165                 170                 175

Asp Val Gly Ala Arg Met Ser Phe His Thr Ala Asp Val Ala Asp Leu
            180                 185                 190

Ala Ser Glu Leu Ala Lys Tyr Asp Val Val Phe Leu Ala Ala Leu Val
        195                 200                 205

Gly Met Ala Ala Glu Asp Lys Ala Lys Val Ile Ala His Leu Gly Ala
    210                 215                 220

His Met Ala Asp Gly Ala Ala Leu Val Val Arg Ser Ala His Gly Ala
225                 230                 235                 240

Arg Gly Phe Leu Tyr Pro Ile Val Asp Pro Gln Asp Ile Gly Arg Gly
                245                 250                 255

Gly Phe Glu Val Leu Ala Val Cys His Pro Asp Asp Val Val Asn
            260                 265                 270

Ser Val Ile Ile Ala Gln Lys Ser Lys Glu Val His Ala Asp Gly Leu
        275                 280                 285

Gly Ser Ala Arg Gly Ala Gly Arg Gln Tyr Ala Arg Gly Thr Val Pro
    290                 295                 300

Val Val Ser Pro Pro Cys Arg Phe Gly Glu Met Val Ala Asp Val Thr
305                 310                 315                 320
```

Gln Asn His Lys Arg Asp Glu Phe Ala Asn Ala Glu Val Ala Phe
            325                 330                 335

<210> SEQ ID NO 6
<211> LENGTH: 1314
<212> TYPE: DNA
<213> ORGANISM: Hordeum vulgare

<400> SEQUENCE: 6

```
ctacttcact cacactagtg cccagaaaga aggctgcaat ggctgcccag aacaacaaca      60
aggatgtcgc tgccctggtg gagaagatca ccgggctcca cgccgccatc gccaagctgc     120
cgtcgctcag cccatccccg gacgtcgacg cgctcttcac cgagctggtc acggcgtgcg     180
ttccccgag ccccgtggac gtgaccaagc tcggccccga ggcgcaggag atgcgggagg      240
gcctcatccg cctctgctcc gaggccgagg ggaagctgga ggcgcactac tccgacatgc     300
tcgccgcctt cgacaacccg ctggatcacc tcggcatctt ccctactac agcaactaca     360
tcaacctcag caagctggag tacgagctcc tggcacgcta cgtccggcgg catcgcccgg     420
cccgcgtcgc gttcatcggc tccggccgc tgccgttcag ctcctttgtc ctggccgcgc      480
gccacctgcc cgacaccatg tttgacaact acgacctttg cggcgcggcc aacgatcgcg     540
ccagcaagct cttccgcgcg gacacggacg tgggtgcccg catgtcgttc cacacggccg     600
acgtcgcgga cctcgccagc gagctcgcca gtacgacgt cgtcttcctg gccgcgctcg      660
tcggcatggc cgccgaggac aaggccaagg tgatcgcgca cctcggcgca cacatggcag     720
acggggcggc cctcgtcgtg cgcagcgcac acggagcgcg cgggttcctg tacccgattg     780
tcgaccccca ggacatcggc cgcggcgggt tcgaggtgct ggccgtgtgc caccccgacg     840
acgacgtggt gaactccgtc atcatcgcac agaagtccaa ggaggtgcat gccgatggac     900
ttggcagcgc gcgtggtgcc ggtcgacagt acgcgcgcgg cacggtgccg gttgtcagcc     960
ccccgtgcag gttcggtgag atggtggcgg atgtgaccca gaaccacaag agagacgagt    1020
ttgccaacgc cgaagtggcc ttttgatcga tcgtcgccaa gggacaataa atgaacgtgg    1080
atgtggtagg gtaatttgcc tacctcgctg cttgatcgct tgcaatatgt gcacattttc    1140
ctactaccgc tgcttatgca tttcaagcca tgtgatgttg gtatccaata agtatgtgt     1200
agggtttaca cgcaaatgtc tttacacctt gtacgtgtaa gtgttgacaa cgatgaattt    1260
cagttcacaa ttaataaata gtataatgga ttcaaaaaaa aaaaaaaaaa aaaa          1314
```

<210> SEQ ID NO 7
<211> LENGTH: 329
<212> TYPE: PRT
<213> ORGANISM: Hordeum vulgare

<400> SEQUENCE: 7

Met Asp Gly Gln Ser Glu Glu Val Asp Ala Leu Val Gln Lys Ile Thr
 1               5                  10                  15

Gly Leu His Ala Ala Ile Ala Lys Leu Pro Ser Leu Ser Pro Ser Pro
            20                  25                  30

Asp Val Asp Ala Leu Phe Thr Asp Leu Val Thr Ala Cys Val Pro Pro
        35                  40                  45

Ser Pro Val Asp Val Thr Lys Leu Ala Pro Glu Ala Gln Ala Met Arg
    50                  55                  60

Glu Gly Leu Ile Arg Leu Cys Ser Glu Ala Glu Gly Lys Leu Glu Ala
65                  70                  75                  80

His Tyr Ser Asp Met Leu Ala Ala Phe Asp Asn Pro Leu Asp His Leu

```
                     85                  90                  95
Gly Val Phe Pro Tyr Tyr Ser Asn Tyr Ile Asn Leu Ser Lys Leu Glu
            100                 105                 110
Tyr Glu Leu Leu Ala Arg Tyr Val Pro Gly Arg His Arg Pro Ala Arg
            115                 120                 125
Val Ala Phe Ile Gly Ser Gly Pro Leu Pro Phe Ser Ser Tyr Val Leu
            130                 135                 140
Ala Ala Arg His Leu Pro Asp Thr Val Phe Asp Asn Tyr Asp Leu Cys
145                 150                 155                 160
Gly Ala Ala Asn Asp Arg Ala Thr Arg Leu Phe Arg Ala Asp Lys Asp
                165                 170                 175
Val Gly Ala Arg Met Ser Phe His Thr Ala Asp Val Ala Asp Leu Thr
            180                 185                 190
Asp Glu Leu Ala Thr Tyr Asp Val Val Phe Leu Ala Ala Leu Val Gly
            195                 200                 205
Met Ala Ala Glu Asp Lys Ala Lys Val Ile Ala His Leu Gly Ala His
210                 215                 220
Met Ala Asp Gly Ala Ala Leu Val Ala Arg His Gly Ala Arg Gly Phe
225                 230                 235                 240
Leu Tyr Pro Ile Val Asp Pro Gln Asp Ile Gly Arg Gly Gly Phe Glu
                245                 250                 255
Val Leu Ala Val Cys His Pro Asp Asp Val Val Asn Ser Val Ile
            260                 265                 270
Ile Ala Gln Lys Ser Asn Asp Val His Glu Tyr Gly Leu Gly Ser Gly
            275                 280                 285
Arg Gly Gly Arg Tyr Ala Arg Gly Thr Val Val Pro Val Ser Pro
290                 295                 300
Pro Cys Arg Phe Gly Glu Met Val Ala Asp Val Thr Gln Lys Arg Glu
305                 310                 315                 320
Glu Phe Ala Asn Ala Glu Val Ala Phe
            325

<210> SEQ ID NO 8
<211> LENGTH: 1249
<212> TYPE: DNA
<213> ORGANISM: Hordeum vulgare

<400> SEQUENCE: 8
ccactaccga ctaccgtagt accgtgcctc agagctcatc actggtcagg taccaagaag     60
acataaaaat ggacggccag agcgaggagg tcgacgccct tgtccagaag atcaccggcc    120
tccacgccgc catcgccaag ctgccctcgc tcagcccgtc cccggacgtc gacgcgctct    180
tcaccgacct ggtcaccgcg tgcgtgcccc cgagcccgt ggacgtgacc aagctcgccc    240
cggaggcgca ggcgatgcgg gagggcctca tccgcctctg ctccgaggcc gagggcaagc    300
tggaggcgca ctactccgac atgctcgccg ccttcgacaa cccgctcgac cacctcggcg    360
tcttccccta ctacagcaac tacatcaacc tcagcaagct tgagtacgag ctcctcgcgc    420
gctacgtgcc cggcaggcat cgcccggccc gcgtcgcctt catcggctcc ggcccgctgc    480
cgttcagctc ctacgtcctc gccgcgcgcc acctgcccga caccgtgttc gacaactacg    540
acctgtgcgg cgcggccaac gaccgcgcga ccaggctgtt ccgcgcggac aaggacgtcg    600
gcgcccgcat gtcgttccac accgccgacg tcgcggacct caccgacgag ctcgctacgt    660
acgacgtcgt cttcctggcc gcgctcgtgg gcatggccgc cgaggacaag gccaaggtga    720
```

-continued

```
tcgcgcacct tggcgcgcac atggcggacg gggcggccct cgttgcgcgg cacggcgcgc      780
gtgggttcct ctacccgatc gtcgatcccc aggacatcgg tcgaggcggg ttcgaggtgc      840
tcgccgtgtg tcaccccgac gacgacgtgg tgaactccgt catcatcgca caaaagagca      900
acgacgtgca cgagtatgga cttggcagcg ggcgtggtgg acggtacgcg cgaggcacgg      960
tggtgccggt ggtcagccca ccctgcaggt tcggcgagat ggtggcagac gtgacccaga     1020
agagagagga gtttgccaac gcggaagtgg ccttctgatt gctgctgaat cgcttgtgat     1080
cgtacgtggt aattttttcta ctactcctcc tcctaccacc acctatcacc tatgtatgca     1140
tttcaagtcg tgtgttgttt gtatccaata atgtaagtga gatgtttaca cgcgcaaaaa     1200
aaaaaaaaaa aaaaaaaaaa aaaaaaaaaa aaaaaaaaaa aaaaaaaaa               1249
```

<210> SEQ ID NO 9
<211> LENGTH: 282
<212> TYPE: PRT
<213> ORGANISM: Hordeum vulgare

<400> SEQUENCE: 9

```
Met Glu Ala Glu Asn Gly Glu Val Ala Ala Leu Val Glu Lys Ile Thr
 1               5                  10                  15

Gly Leu His Ala Ala Ile Ser Lys Leu Pro Ala Leu Ser Pro Ser Pro
             20                  25                  30

Gln Val Asp Ala Leu Phe Thr Glu Leu Val Ala Ala Cys Val Pro Ser
         35                  40                  45

Ser Pro Val Asp Val Thr Lys Leu Gly Pro Glu Ala Gln Glu Met Arg
     50                  55                  60

Gln Asp Leu Ile Arg Leu Cys Ser Ala Ala Glu Gly Leu Leu Glu Ala
 65                  70                  75                  80

His Tyr Ser Asp Met Leu Thr Ala Leu Asp Ser Pro Leu Asp His Leu
                 85                  90                  95

Gly Arg Phe Pro Tyr Phe Asp Asn Tyr Val Asn Leu Ser Lys Leu Glu
            100                 105                 110

His Asp Leu Leu Ala Gly His Val Ala Ala Pro Ala Arg Val Ala Phe
        115                 120                 125

Ile Gly Ser Gly Pro Leu Pro Phe Ser Ser Leu Phe Leu Ala Thr Tyr
    130                 135                 140

His Leu Pro Asp Thr Arg Phe Asp Asn Tyr Asp Arg Cys Ser Val Ala
145                 150                 155                 160

Asn Gly Arg Ala Met Lys Leu Val Gly Ala Ala Asp Glu Gly Val Arg
                165                 170                 175

Ser Arg Met Ala Phe His Thr Ala Glu Val Thr Asp Leu Thr Ala Glu
            180                 185                 190

Leu Gly Ala Tyr Asp Val Val Phe Leu Ala Ala Leu Val Gly Met Thr
        195                 200                 205

Ser Lys Glu Lys Ala Asp Ala Ile Ala His Leu Gly Lys His Met Ala
    210                 215                 220

Asp Gly Ala Val Leu Val Arg Glu Ala Leu His Gly Ala Arg Ala Phe
225                 230                 235                 240

Leu Tyr Pro Val Glu Leu Asp Asp Val Gly Arg Gly Gly Phe Gln
                245                 250                 255

Val Leu Ala Val His His Pro Ala Gly Asp Glu Val Phe Asn Ser Phe
            260                 265                 270

Ile Val Ala Arg Lys Val Lys Met Ser Ala
        275                 280
```

<210> SEQ ID NO 10
<211> LENGTH: 1044
<212> TYPE: DNA
<213> ORGANISM: Hordeum vulgare

<400> SEQUENCE: 10

```
gtgacatgga ggccgaaaac ggcgaggtgg ctgctctggt cgagaagatc accggtctcc    60
acgccgccat ctccaagctc ccggcactaa gcccgtctcc tcaagtcgac gcgctcttca   120
ccgagctggt tgcggcgtgc gtcccatcaa gcccggtgga cgtgaccaag ctcggcccgg   180
aggcgcagga gatgcggcag gacctcatcc gtctctgctc ggccgccgag gggctgctcg   240
aggcgcacta ctccgacatg ctcaccgcgt tggacagccc gctcgaccac ctcggccgct   300
tcccttactt cgacaactac gtcaacctca gcaagctcga gcacgatctt ctggcaggtc   360
acgtggcggc cccggcccgc gtggcgttca tcgggtcggg gccactgccg ttcagctcgc   420
tcttccttgc gacgtaccac ctgccggaca cccggttcga caactacgac cggtgcagcg   480
tggcgaatgg ccgggcgatg aagctggtcg gcgcggcgga cgaggcgtg cgatcacgca   540
tggcgttcca cacggccgaa gtcacggacc tcacggctga gctcggcgct tacgacgtgg   600
tcttcctggc cgcgctcgtg ggaatgacgt ccaaggagaa ggccgacgcc atagcgcact   660
gggggaagca catggcagat ggggcggtgc tcgtgcgcga agcgctgcac ggggcgcgag   720
cgttcctgta tcctgtcgtg gagctggacg atgtcgggcg tggtgggttc caagtgctgg   780
ccgtgcacca ccctgcaggc gatgaggtgt tcaactcatt catagttgcc cggaaggtga   840
aaatgagtgc ttaaattaag aaagggtga gcctgtctgc ttgtgcaaat ggtgtctcac   900
attgataata accagatgat accctgcaca ttgatgggg tactgcagta tgtttcaatg   960
aggtctggtt gtatcaaata tgagtatttg gcttaataat atcagcgaat atgtttcgat  1020
taaaaaaaaa aaaaaaaaaa aaaa                                         1044
```

<210> SEQ ID NO 11
<211> LENGTH: 328
<212> TYPE: PRT
<213> ORGANISM: Hordeum vulgare

<400> SEQUENCE: 11

```
Met Asp Ala Gln Asn Lys Glu Val Asp Ala Leu Val Gln Lys Ile Thr
  1               5                  10                  15

Gly Leu His Ala Ala Ile Ala Lys Leu Pro Ser Leu Ser Pro Ser Pro
             20                  25                  30

Asp Val Asp Ala Leu Phe Thr Asp Leu Val Thr Ala Cys Val Pro Pro
         35                  40                  45

Ser Pro Val Asp Val Thr Lys Leu Gly Ser Glu Ala Gln Glu Met Arg
     50                  55                  60

Glu Gly Leu Ile Arg Leu Cys Ser Glu Ala Glu Gly Lys Leu Glu Ala
 65                  70                  75                  80

His Tyr Ser Asp Met Leu Ala Ala Phe Asp Asn Pro Leu Asp His Leu
                 85                  90                  95

Gly Met Phe Pro Tyr Tyr Ser Asn Tyr Ile Asn Leu Ser Lys Leu Glu
            100                 105                 110

Tyr Glu Leu Leu Ala Arg Tyr Val Pro Gly Gly Ile Ala Arg Pro Ala
        115                 120                 125

Val Ala Phe Ile Gly Ser Gly Pro Leu Pro Phe Ser Ser Tyr Val Leu
    130                 135                 140
```

-continued

```
Ala Ala Arg His Leu Pro Asp Ala Met Phe Asp Asn Tyr Asp Leu Cys
145                 150                 155                 160

Ser Ala Ala Asn Asp Arg Ala Ser Lys Leu Phe Arg Ala Asp Lys Asp
                165                 170                 175

Val Gly Ala Arg Met Ser Phe His Thr Ala Asp Val Ala Asp Leu Thr
            180                 185                 190

Arg Glu Leu Ala Ala Tyr Asp Val Val Phe Leu Ala Ala Leu Val Gly
        195                 200                 205

Met Ala Ala Glu Asp Lys Ala Lys Val Ile Pro His Leu Gly Ala His
210                 215                 220

Met Ala Asp Gly Ala Ala Leu Val Val Arg Ser Ala Gln Ala Arg Gly
225                 230                 235                 240

Phe Leu Tyr Pro Ile Val Asp Pro Gln Asp Ile Gly Arg Gly Gly Phe
                245                 250                 255

Glu Val Leu Ala Val Cys His Pro Asp Asp Val Val Asn Ser Val
                260                 265                 270

Ile Ile Ala His Lys Ser Lys Asp Val His Ala Asn Glu Arg Pro Asn
275                 280                 285

Gly Arg Gly Gly Gln Tyr Arg Gly Ala Val Pro Val Val Ser Pro Pro
290                 295                 300

Cys Arg Phe Gly Glu Met Val Ala Asp Val Thr His Lys Arg Glu Glu
305                 310                 315                 320

Phe Thr Asn Ala Glu Val Ala Phe
                325
```

<210> SEQ ID NO 12
<211> LENGTH: 1352
<212> TYPE: DNA
<213> ORGANISM: Hordeum vulgare

<400> SEQUENCE: 12

```
ctccacttcg ctcctgtgcc tcaggtagcc acaacataca gtattaaaat ggatgcccag      60
aacaaggagg ttgatgccct ggtccagaag atcaccggcc tccacgccgc catcgccaag     120
ctgccgtccc tcagcccatc acccgacgtc gacgcgctct tcaccgacct ggtcaccgcg     180
tgcgtccccc cgagccccgt ggacgtgacc aagctcgggt cggaggcgca ggagatgcgg     240
gagggcctca tccgcctctg ctccgaggcc gaggggaagc tggaggcgca ctactccgac     300
atgctggccg ccttcgacaa cccgctcgac cacctcggca tgttcccctt ctacagcaac     360
tacatcaacc tcagcaagct ggagtacgag ctcctggcgc gctacgtgcc gggcggcatc     420
gcccggcccg ctgtcgcgtt catcggctcc ggcccgctgc cgttcagctc ctacgtcctc     480
gccgctcgcc acctgcccga cgccatgttc gacaactacg acctgtgtag cgcggccaac     540
gaccgtgcga gcaagctgtt ccgcgcggac aaggacgtgg gcgcccgcat gtctttccac     600
accgccgacg tagcggacct cacccgcgag ctcgccgcgt acgacgtcgt cttcctggcc     660
gcgctcgtgg gcatggctgc cgaggacaag gccaaggtga ttccgcacct cggcgcgcac     720
atggcggacg gggcggccct cgtcgtgcgc agtgcgcagg cacgtgggtt cctctacccg     780
atcgtcgatc cccaggacat cggtcgaggc gggtttgagg tgctggccgt tgtgcacccc     840
gacgatgacg tggtgaactc cgtcatcatc gcacacaagt ccaaggacgt gcatgccaat     900
gaacgtccca acgggcgtgg tggacagtac cggggcgcgg taccggtggt cagcccgccg     960
tgcaggttcg gtgagatggt ggcggacgtg acccacaaga gagaggagtt caccaacgcg    1020
```

-continued

```
gaagtggcct tctgatcgtt gcgagggaat gaaaatgaag gtggacgtgt gtggtcagca      1080
tccatacgtg gctgcctgct tcatcgcttg caatcgtact actacctacc tatgcagttc      1140
aagtcatgtg ttgtcaatgt aagtgtgatt tttacactag tctatgaaag gcagggcaga      1200
cgagggtagt gtgccaagta acagtgtgtc attataggtg taagtgttga gaataagacc      1260
atttttgttc acaaatagta tgatgtaatc ggtgtcatat tcgtattgag tacatttgtc      1320
aagttggttg ctaaaaaaaa aaaaaaaaaa aa                                    1352
```

<210> SEQ ID NO 13
<211> LENGTH: 329
<212> TYPE: PRT
<213> ORGANISM: Hordeum vulgare

<400> SEQUENCE: 13

```
Met Asp Ala Gln Ser Lys Glu Val Asp Ala Leu Val Gln Lys Ile Thr
  1               5                  10                  15

Gly Leu His Ala Ala Ile Ala Lys Leu Pro Ser Leu Ser Pro Ser Pro
                 20                  25                  30

Asp Val Asp Ala Leu Phe Thr Asp Leu Val Thr Ala Cys Val Pro Pro
             35                  40                  45

Ser Pro Val Asp Val Thr Lys Leu Ala Pro Glu Ala Gln Ala Met Arg
         50                  55                  60

Glu Gly Leu Ile Arg Leu Cys Ser Glu Ala Glu Gly Lys Leu Glu Ala
 65                  70                  75                  80

His Tyr Ser Asp Met Leu Ala Ala Phe Asp Asn Pro Leu Asp His Leu
                 85                  90                  95

Gly Val Phe Pro Tyr Tyr Ser Asn Tyr Ile Asn Leu Ser Lys Leu Glu
                100                 105                 110

Tyr Glu Leu Leu Ala Arg Tyr Val Pro Gly Gly Ile Ala Pro Ala Arg
            115                 120                 125

Val Ala Phe Ile Gly Ser Gly Pro Leu Pro Phe Ser Ser Tyr Val Leu
        130                 135                 140

Ala Ala Arg His Leu Pro Asp Thr Val Phe Asp Asn Tyr Val Pro Val
145                 150                 155                 160

Arg Ala Ala Asn Asp Arg Ala Thr Arg Leu Phe Arg Ala Asp Lys Asp
                165                 170                 175

Val Gly Ala Arg Met Ser Phe His Thr Ala Asp Val Ala Asp Leu Thr
            180                 185                 190

Asp Glu Leu Ala Thr Tyr Asp Val Val Phe Leu Ala Ala Leu Val Gly
        195                 200                 205

Met Ala Ala Glu Asp Lys Gly Gln Gly Asp Pro His Leu Gly Ala His
    210                 215                 220

Met Ala Asp Gly Ala Ala Leu Val Arg Ser Ala His Gly Ala Arg Gly
225                 230                 235                 240

Phe Leu Tyr Pro Ile Val Asp Pro Gln Asp Ile Gly Arg Gly Gly Phe
                245                 250                 255

Glu Val Leu Ala Val Cys His Pro Asp Asp Val Val Asn Ser Val
            260                 265                 270

Ile Ile Ala Gln Lys Ser Lys Asp Met Phe Ala Asn Gly Pro Arg Asn
        275                 280                 285

Gly Cys Gly Gly Arg Tyr Ala Arg Gly Thr Val Pro Val Val Ser Pro
    290                 295                 300

Pro Cys Arg Phe Gly Glu Met Val Ala Asp Val Thr Gln Lys Arg Glu
305                 310                 315                 320
```

Glu Phe Ala Lys Ala Glu Val Ala Phe
            325

<210> SEQ ID NO 14
<211> LENGTH: 1371
<212> TYPE: DNA
<213> ORGANISM: Hordeum vulgare
<220> FEATURE:
<221> NAME/KEY: modified_base
<222> LOCATION: (8)
<223> OTHER INFORMATION: a, c, g, t, unknown or other

<400> SEQUENCE: 14

```
ggagcggnac gcgtggcgga ggtgggcact accgtagtac cgtgcctcag agctcatcac      60
tggtcaggta ccaagaagac ataaaaatgg acgcccagag caaggaggtc gacgcccttg     120
tccagaagat caccggcctc cacgccgcca tcgccaagct gccctcgctc agcccgtccc     180
cggacgtcga cgcgctcttc accgacctgg tcaccgcgtg cgtgccccg agcccgtgg      240
acgtgaccaa gctcgccccg gaggcgcagg cgatgcggga gggcctcatc cgcctctgct     300
ccgaggccga gggcaagctg gaggcgcact actccgacat gctcgccgcc ttcgacaacc     360
cgctcgacca cctcggcgtc ttcccctact acagcaacta catcaacctc agcaagctcg     420
agtacgagct cctcgcgcgc tacgtgcccg gcggcatcgc cccggcccgc gtcgccttca     480
tcggctccgg cccgctcccg ttcagctcct acgtcctcgc cgcgcgccac ctgcccgaca     540
ccgtgttcga caactacgta cctgtgcgcg cggccaacga ccgcgcgacc aggctgttcc     600
gcgcggacaa ggacgtcggc gcccgcatgt cgttccacac cgccgacgtc gcggacctca     660
ccgacgagct cgctacgtac gacgtcgtct tcctggccgc gctcgtgggc atggccgccg     720
aggacaaggg ccaaggtgat ccgcaccttg gcgcgcacat ggcggacggg gcggccctcg     780
tccgcagcgc gcacggggcg cgtgggttcc tctacccgat cgtcgatccc caagacattg     840
gtcgaggcgg gttcgaggtg ctcgccgtgt gtcacccga cgacgacgtg gtgaactccg     900
tcatcatcgc gcagaagtct aaggacatgt ttgccaatgg acctcgcaac gggtgtggtg     960
gacggtacgc gcgaggcacg gtgccggtgg tcagcccgcc ctgcaggttc ggcgagatgg    1020
tggcagacgt gacccagaag agagaggagt ttgccaaggc ggaagtggcc ttctgattgc    1080
tgcgaggtca ccatccgtat gccgctgcta cctttcaata tcttgcaatc gtaggtggcg    1140
attttcctac tcttgttacg acctttcaaa tcatatgttg tttgtaccca ataatgtaag    1200
tgtgttgctt acacgcgcat gtcttgtaca ctcggtctct agaaggcagg gcagatcaag    1260
agactgtgca aaggaaaaga aatgtgtgtt gttgtaggtg tatgagttgg gagtaagatg    1320
attctagttc acaaaaaaaa aaaaaaaaaa aaaaaaaaaa a                         1371
```

<210> SEQ ID NO 15
<211> LENGTH: 324
<212> TYPE: PRT
<213> ORGANISM: Oryza sativa

<400> SEQUENCE: 15

Met Glu Ala Gln Asn Gln Glu Val Ala Ala Leu Val Glu Lys Ala Gly
1               5                   10                  15

Leu His Ala Ala Ser Lys Leu Pro Ser Leu Ser Pro Ser Ala Glu Val
            20                  25                  30

Asp Ala Leu Phe Thr Asp Leu Val Thr Ala Cys Val Pro Ala Ser Pro
        35                  40                  45

-continued

```
Val Asp Val Ala Lys Leu Gly Pro Glu Ala Gln Ala Met Arg Glu Glu
        50                  55                  60

Leu Arg Leu Cys Ser Ala Ala Glu Gly His Leu Glu Ala His Tyr Ala
 65                  70                  75                  80

Asp Met Leu Ala Ala Phe Asp Asn Pro Leu Asp His Leu Ala Arg Phe
                 85                  90                  95

Pro Tyr Tyr Gly Asn Tyr Val Asn Leu Ser Lys Leu Glu Tyr Asp Leu
            100                 105                 110

Leu Val Arg Tyr Val Pro Gly Ala Pro Thr Arg Val Ala Phe Val Gly
        115                 120                 125

Ser Gly Pro Leu Pro Phe Ser Ser Leu Val Leu Ala Ala His His Leu
130                 135                 140

Pro Asp Ala Val Phe Asp Asn Tyr Asp Arg Cys Gly Ala Ala Asn Glu
145                 150                 155                 160

Arg Ala Arg Arg Leu Phe Arg Gly Ala Asp Glu Gly Leu Gly Ala Arg
                165                 170                 175

Met Ala Phe His Thr Ala Asp Val Ala Thr Leu Thr Gly Glu Leu Gly
            180                 185                 190

Ala Tyr Asp Val Val Phe Leu Ala Ala Leu Val Gly Met Ala Ala Glu
        195                 200                 205

Glu Lys Ala Gly Val Ala His Leu Gly Ala His Met Ala Asp Gly Ala
210                 215                 220

Ala Leu Val Val Arg Thr Ala His Gly Ala Arg Gly Phe Leu Tyr Pro
225                 230                 235                 240

Val Asp Pro Glu Asp Val Arg Arg Gly Phe Asp Val Leu Ala Val
                245                 250                 255

Cys His Pro Glu Asp Glu Val Asn Ser Val Ala Arg Lys Val Gly
            260                 265                 270

Ala Ala Ala Ala Ala Ala Ala Arg Arg Asp Glu Leu Ala Asp Ser
        275                 280                 285

Arg Gly Val Val Leu Pro Val Val Gly Pro Pro Ser Thr Cys Cys Lys
290                 295                 300

Val Glu Ala Ser Ala Val Glu Lys Ala Glu Glu Phe Ala Ala Asn Lys
305                 310                 315                 320

Glu Leu Ser Val
```

<210> SEQ ID NO 16
<211> LENGTH: 1372
<212> TYPE: DNA
<213> ORGANISM: Oryza sativa

<400> SEQUENCE: 16

| | | |
|---|---|---|
| ctccatttgg ttgtcatttt caactataat ccaccacaac tcgtgcaaca tcagctcact | 60 |
| cgtgttccca accgcgacaa agcttcacag atggaggctc agaaccaaga ggtcgctgcc | 120 |
| ctggtcgaga agatcgccgg cctccacgcc gccatctcca agctgccgtc gctgagccca | 180 |
| tccgccgagg tggacgcgct cttcaccgac ctcgtcacgg cgtgcgtccc ggcgagcccc | 240 |
| gtcgacgtgg ccaagctcgg cccggaggcg caggcgatgc gggaggagct catccgcctc | 300 |
| tgctccgccg ccgagggcca cctcgaggcg cactacgccg acatgctcgc cgccttcgac | 360 |
| aacccgctcg accacctcgc cgcttcccg tactacggca actacgtcaa cctgagcaag | 420 |
| ctggagtacg acctcctcgt ccgctacgtc ccggcattg ccccaccccg cgtcgccttc | 480 |
| gtcgggtcgg gcccgctgcc gttcagctcc ctcgtgctcg ctgcgcacca cctgccggac | 540 |

-continued

```
gcggtgttcg acaactacga ccggtgcggc gcggccaacg agcgggcgag gaggctgttc      600
cgcggcgccg acgagggcct cggcgcgcgc atggcgttcc acaccgccga cgtggcgacc      660
ctgacggggg agctcggcgc gtacgacgtc gtgttcctgg cggcgctcgt gggcatggcg      720
gccgaggaga aggccgggt gatcgcgcac ctgggcgcgc atggcggga cggcgcggcg      780
ctcgtcgtgc ggacggcgca cggggcgcgc ggttcctgt acccgatcgt cgatcccgag      840
gacgtcaggc gtggcgggtt cgacgttctg gcggtgtgcc acccggagga cgaggtgatc      900
aactccgtca tcgtcgcccg caaggtcggt gccgccgccg ccgccgccgc ggcgcgcaga      960
gacgagctcg cggactcgcg cggcgtggtt ctgccggtgg tcgggccgcc gtccacgtgc     1020
tgcaaggtgg aggcgagcgc ggttgagaag cagaagagt ttgccgccaa caaggagctg     1080
tccgtctaac agccggacga tcgaaaggcg cactatatta tggcaataaa tcatttgatt     1140
atacttatgc tgcatttgcg aagctaaggt atactatgca agccatatgt ttgtgttcgt     1200
acgtgttgtt tgggacgtac agttgtgttg ttgtacgtcg tgaagtactg aagtgttcac     1260
agtagatcac aagttcacag caatcaatga ggaccctgta agccagtgta aacgaggaac     1320
atgccatctg tgtatgacag tgagaaatta tataagaaaa acattttgtg ac             1372
```

<210> SEQ ID NO 17
<211> LENGTH: 320
<212> TYPE: PRT
<213> ORGANISM: Arabidopsis thaliana

<400> SEQUENCE: 17

```
Met Ala Cys Gln Asn Asn Leu Val Val Lys Gln Ile Ile Asp Leu Tyr
  1               5                  10                  15

Asp Gln Ile Ser Lys Leu Lys Ser Leu Lys Pro Ser Lys Asn Val Asp
             20                  25                  30

Thr Leu Phe Gly Gln Leu Val Ser Thr Cys Leu Pro Thr Asp Thr Asn
         35                  40                  45

Ile Asp Val Thr Asn Met Cys Glu Glu Val Lys Asp Met Arg Ala Asn
     50                  55                  60

Leu Ile Lys Leu Cys Gly Glu Ala Glu Gly Tyr Leu Glu Gln His Phe
 65                  70                  75                  80

Ser Thr Ile Leu Gly Ser Leu Gln Glu Asp Gln Asn Pro Leu Asp His
                 85                  90                  95

Leu His Ile Phe Pro Tyr Tyr Ser Asn Tyr Leu Lys Leu Gly Lys Leu
            100                 105                 110

Glu Phe Asp Leu Leu Ser Gln His Ser Ser His Val Pro Thr Lys Ile
        115                 120                 125

Ala Phe Val Gly Ser Gly Pro Met Pro Leu Thr Ser Ile Val Leu Ala
    130                 135                 140

Lys Phe His Leu Pro Asn Thr Thr Phe His Asn Phe Asp Ile Asp Ser
145                 150                 155                 160

His Ala Asn Thr Leu Ala Ser Asn Leu Val Ser Arg Asp Pro Asp Leu
                165                 170                 175

Ser Lys Arg Met Ile Phe His Thr Thr Asp Val Leu Asn Ala Thr Glu
            180                 185                 190

Ala Leu Asp Gln Tyr Asp Val Val Phe Leu Ala Ala Leu Val Gly Met
        195                 200                 205

Asp Lys Glu Ser Lys Val Lys Ala Ile Glu His Leu Glu Lys His Met
    210                 215                 220

Ala Pro Gly Ala Val Leu Met Leu Arg Arg Ala His Ala Leu Arg Ala
```

```
                    225                 230                 235                 240

Phe Leu Tyr Pro Ile Val Asp Ser Ser Asp Leu Lys Gly Phe Gln Leu
                    245                 250                 255

Leu Thr Ile Tyr His Pro Thr Asp Asp Val Val Asn Ser Val Ile
                260                 265                 270

Ala Arg Lys Leu Gly Gly Pro Thr Thr Pro Gly Val Asn Gly Thr Arg
                    275                 280                 285

Gly Cys Met Phe Met Pro Cys Asn Cys Ser Lys Ile His Ala Ile Met
                290                 295                 300

Asn Asn Arg Gly Lys Lys Asn Met Ile Glu Glu Phe Ser Thr Ile Glu
    305                 310                 315                 320

<210> SEQ ID NO 18
<211> LENGTH: 963
<212> TYPE: DNA
<213> ORGANISM: Arabidopsis thaliana

<400> SEQUENCE: 18
atggcttgcc aaaacaatct cgttgtgaag caaatcatcg acttgtacga ccaaatctca    60
aagctcaaga gcttaaaacc ttccaaaaat gtcgacactt tgttcggaca actcgtgtcc   120
acgtgcttac ccacggatac aaacatcgat gtcacaaata tgtgtgaaga agtcaaagac   180
atgagagcta atctcatcaa gctttgtggt gaagccgaag gttatttgga gcaacacttc   240
tccacaattt tgggatcttt acaagaagac caaaacccac ttgaccattt acacatcttt   300
ccttactact ccaactacct caagctaggc aagctcgagt cgatctcct gagccaacac    360 tcaagccatg tccccaccaa gattgccttc gtgggttcgg gtccgatgcc tctcacatcc   420
atcgtattgg ccaagtttca cctccccaac acgacgttcc acaactttga catcgactca   480
cacgcaaaca cactcgcttc aaacctcgtc tctcgcgacc cggacctctc aaaacgcatg   540
atcttccaca acgacgt actaaacgca accgaagccc ttgaccaata tgacgtcgtt    600
ttcttagcgg cgcttgtagg gatggacaaa gagtcaaagg tcaaagccat cgagcacttg   660
gagaaacaca tggctcctgg agctgttctt atgctaagga gggctcatgc tctcagagct   720
ttcttatatc aatcgttga ctcgtctgat ctcaaaggct tcaactctt gaccatctat     780 catccaaccg atgacgtggt taactcggtt gtgatcgcac gtaagctcgg tggtccgacc   840
acgcccgggg ttaatggtac tcgtggatgc atgtttatgc cttgtaactg ctccaagatt   900
cacgcgatca tgaacaaccg tggtaagaag aatatgatcg aggagtttag taccatcgag   960
taa                                                                  963

<210> SEQ ID NO 19
<211> LENGTH: 320
<212> TYPE: PRT
<213> ORGANISM: Arabidopsis thaliana

<400> SEQUENCE: 19

Met Ala Cys Gln Asn Asn Leu Val Val Lys Gln Ile Met Asp Leu Tyr
    1                   5                   10                  15

Asn Gln Ile Ser Asn Leu Glu Ser Leu Lys Pro Ser Lys Asn Val Asp
                20                  25                  30

Thr Leu Phe Arg Gln Leu Val Ser Thr Cys Leu Pro Thr Asp Thr Asn
                35                  40                  45

Ile Asp Val Thr Glu Ile His Asp Glu Lys Val Lys Asp Met Arg Ser
    50                  55                  60
```

-continued

| | | | | | | | | | | | | | | |
|---|---|---|---|---|---|---|---|---|---|---|---|---|---|---|
|His|Leu|Ile|Lys|Leu|Cys|Gly|Glu|Ala|Glu|Gly|Tyr|Leu|Glu|Gln|His|
|65| | | |70| | | | |75| | | | |80|

Phe Ser Ala Ile Leu Gly Ser Phe Glu Asp Asn Pro Leu Asn His Leu
                85                  90                  95

His Ile Phe Pro Tyr Tyr Asn Asn Tyr Leu Lys Leu Gly Lys Leu Glu
            100                 105                 110

Phe Asp Leu Leu Ser Gln His Thr Thr His Val Pro Thr Lys Val Ala
        115                 120                 125

Phe Ile Gly Ser Gly Pro Met Pro Leu Thr Ser Ile Val Leu Ala Lys
    130                 135                 140

Phe His Leu Pro Asn Thr Thr Phe His Asn Phe Asp Ile Asp Ser His
145                 150                 155                 160

Ala Asn Thr Leu Ala Ser Asn Leu Val Ser Arg Asp Ser Asp Leu Ser
                165                 170                 175

Lys Arg Met Ile Phe His Thr Thr Asp Val Leu Asn Ala Lys Glu Gly
            180                 185                 190

Leu Asp Gln Tyr Asp Val Val Phe Leu Ala Ala Leu Val Gly Met Asp
        195                 200                 205

Lys Glu Ser Lys Val Lys Ala Ile Glu His Leu Glu Lys His Met Ala
    210                 215                 220

Pro Gly Ala Val Val Met Leu Arg Ser Ala His Gly Leu Arg Ala Phe
225                 230                 235                 240

Leu Tyr Pro Ile Val Asp Ser Cys Asp Leu Lys Gly Phe Glu Val Leu
                245                 250                 255

Thr Ile Tyr His Pro Ser Asp Asp Val Val Asn Ser Val Val Ile Ala
            260                 265                 270

Arg Lys Leu Gly Gly Ser Asn Gly Ala Arg Gly Ser Gln Ile Gly Arg
        275                 280                 285

Cys Val Val Met Pro Cys Asn Cys Ser Lys Val His Ala Ile Leu Asn
    290                 295                 300

Asn Arg Gly Met Glu Lys Asn Leu Ile Glu Glu Phe Ser Ala Ile Glu
305                 310                 315                 320

<210> SEQ ID NO 20
<211> LENGTH: 963
<212> TYPE: DNA
<213> ORGANISM: Arabidopsis thaliana

<400> SEQUENCE: 20
atggcttgcc aaaacaatct cgttgtgaag caaatcatgg acttatacaa ccaaatctca      60
aacctcgaga gcttaaaacc atccaagaat gtcgacactt tgttcagaca acttgtgtcc     120
acgtgcttac caacggacac gaacatcgat gtcacagaga tacacgatga aaaagtcaaa     180
gacatgagat ctcatctcat caagctttgt ggtgaagccg aaggttattt agagcaacac     240
ttttcagcaa tcttaggctc ttttgaagac aaccctctaa accatttaca catcttcccc     300
tattacaaca actatctcaa actaggcaaa ctcgaattcg atctcctttc tcagcacaca     360
acccatgtcc cgaccaaagt cgcctttatt ggttccggtc cgatgccact tacttccatc     420
gtcttggcca agttccacct ccccaacaca acgttccaca cttcgacat cgactcacac     480 gccaacacac tcgcttcaaa cctcgtttct cgtgattctg acctttccaa acgcatgatt     540
ttccacacaa ctgatgtatt aaacgctaag gaggggttag accaatacga tgttgttttc     600
ttggcagctc ttgttgggat ggataaagag tcaaaggtca aagctattga gcatttagag     660
aagcatatgg cccctggagc tgtggtgatg ctaagaagtg ctcatggtct tagagctttc     720

-continued

```
ttgtatccaa tcgttgactc ttgtgatctt aaagggtttg aggtgttaac catttatcat    780
ccgtctgacg acgtggttaa ttcggtggtc atcgcacgta agcttggtgg ttcaaatgga    840
gctcgaggca gccagatcgg acggtgtgtg gttatgcctt gtaattgctc taaggtccac    900
gcgatcttga acaatcgtgg tatggagaag aatttgatcg aggagtttag tgccatcgag    960
taa                                                                   963
```

<210> SEQ ID NO 21
<211> LENGTH: 320
<212> TYPE: PRT
<213> ORGANISM: Arabidopsis thaliana

<400> SEQUENCE: 21

```
Met Gly Cys Gln Asp Glu Gln Leu Val Gln Thr Ile Cys Asp Leu Tyr
 1               5                  10                  15

Glu Lys Ile Ser Lys Leu Glu Ser Leu Lys Pro Ser Glu Asp Val Asn
             20                  25                  30

Ile Leu Phe Lys Gln Leu Val Ser Thr Cys Ile Pro Pro Asn Pro Asn
         35                  40                  45

Ile Asp Val Thr Lys Met Cys Asp Arg Val Gln Glu Ile Arg Leu Asn
     50                  55                  60

Leu Ile Lys Ile Cys Gly Leu Ala Glu Gly His Leu Glu Asn His Phe
 65                  70                  75                  80

Ser Ser Ile Leu Thr Ser Tyr Gln Asp Asn Pro Leu His His Leu Asn
             85                  90                  95

Ile Phe Pro Tyr Tyr Asn Asn Tyr Leu Lys Leu Gly Lys Leu Glu Phe
        100                 105                 110

Asp Leu Leu Glu Gln Asn Leu Asn Gly Phe Val Pro Lys Ser Val Ala
    115                 120                 125

Phe Ile Gly Ser Gly Pro Leu Pro Leu Thr Ser Ile Val Leu Ala Ser
130                 135                 140

Phe His Leu Lys Asp Thr Ile Phe His Asn Phe Asp Ile Asp Pro Ser
145                 150                 155                 160

Ala Asn Ser Leu Ala Ser Leu Val Ser Ser Asp Pro Asp Ile Ser
            165                 170                 175

Gln Arg Met Phe Phe His Thr Val Asp Ile Met Asp Val Thr Glu Ser
        180                 185                 190

Leu Lys Ser Phe Asp Val Val Phe Leu Ala Ala Leu Val Gly Met Asn
    195                 200                 205

Lys Glu Glu Lys Val Lys Val Ile Glu His Leu Gln Lys His Met Ala
210                 215                 220

Pro Gly Ala Val Leu Met Leu Arg Ser Ala His Gly Pro Arg Ala Phe
225                 230                 235                 240

Leu Tyr Pro Ile Val Glu Pro Cys Asp Leu Gln Gly Phe Glu Val Leu
            245                 250                 255

Ser Ile Tyr His Pro Thr Asp Asp Val Ile Asn Ser Val Val Ile Ser
        260                 265                 270

Lys Lys His Pro Val Val Ser Ile Gly Asn Val Gly Pro Asn Ser
    275                 280                 285

Cys Leu Leu Lys Pro Cys Asn Cys Ser Lys Thr His Ala Lys Met Asn
290                 295                 300

Lys Asn Met Met Ile Glu Glu Phe Gly Ala Arg Glu Glu Gln Leu Ser
305                 310                 315                 320
```

<210> SEQ ID NO 22
<211> LENGTH: 963
<212> TYPE: DNA
<213> ORGANISM: Arabidopsis thaliana

<400> SEQUENCE: 22

| | | | | | |
|---|---|---|---|---|---|
| atgggttgcc | aagacgaaca | attggtgcaa | acaatatgcg | atctctacga | aaagatctca | 60 |
| aagcttgaga | gtctaaaacc | atccgaagat | gtcaacattc | tcttcaagca | gctcgtttcc | 120 |
| acatgcatac | caccaaaccc | taacatcgat | gtcaccaaga | tgtgtgacag | agtccaagag | 180 |
| attcgactta | atctcatcaa | gatttgtggt | ctagccgaag | gtcacttaga | aaccatttc | 240 |
| tcttcgatct | tgacctctta | ccaagacaac | ccacttcatc | atttaaacat | tttcccttat | 300 |
| tacaacaact | atttgaaact | cggaaagctc | gagttcgacc | tcctcgaaca | aaacctaaat | 360 |
| ggctttgtcc | caaagagtgt | ggctttcatt | ggatctggtc | ctcttcctct | cacttccatc | 420 |
| gttcttgctt | cattccatct | caaagacaca | atctttcaca | actttgacat | cgacccatca | 480 |
| gcgaactcac | tcgcttctct | tctggttttcc | tctgatccag | acatctctca | acgcatgttc | 540 |
| ttccacaccg | ttgatataat | ggacgtgaca | gagagcttaa | agagctttga | tgtcgtgttt | 600 |
| ctagctgctc | ttgttggaat | gaacaaagag | gagaaagtta | aagtgatcga | gcatctgcag | 660 |
| aaacacatgg | ctcctggtgc | tgtgctcatg | cttaggagtg | ctcatggtcc | gagagcgttt | 720 |
| ctttatccga | tcgttgagcc | gtgtgatctt | caggggttcg | aggttttgtc | tatttatcac | 780 |
| ccaacagatg | atgttatcaa | ctccgtggtg | atctctaaaa | agcatccagt | tgtttcaatt | 840 |
| gggaatgttg | gtggtcctaa | ttcatgcttg | ctcaagcctt | gcaactgttc | caagacccac | 900 |
| gcgaaaatga | acaagaacat | gatgatcgag | gagttcggag | ctagggagga | acagttgtct | 960 |
| taa | | | | | | 963 |

<210> SEQ ID NO 23
<211> LENGTH: 32
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (3)
<223> OTHER INFORMATION: Variable amino acid residue
<220> FEATURE:
<221> NAME/KEY: MOD_RES
<222> LOCATION: (9)
<223> OTHER INFORMATION: Variable amino acid residue
<220> FEATURE:
<221> NAME/KEY: MOD_RES
<222> LOCATION: (16)
<223> OTHER INFORMATION: Variable amino acid residue
<220> FEATURE:
<221> NAME/KEY: MOD_RES
<222> LOCATION: (19)
<223> OTHER INFORMATION: Variable amino acid residue
<220> FEATURE:
<221> NAME/KEY: MOD_RES
<222> LOCATION: (24)
<223> OTHER INFORMATION: Variable amino acid residue

<400> SEQUENCE: 23

Leu Pro Xaa Leu Ser Pro Ser Pro Xaa Val Asp Arg Leu Phe Thr Xaa
 1               5                  10                  15

Leu Val Xaa Ala Cys Val Pro Xaa Ser Pro Val Asp Val Thr Lys Leu
                20                  25                  30

```
<210> SEQ ID NO 24
<211> LENGTH: 16
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (7)
<223> OTHER INFORMATION: Variable amino acid residue
<220> FEATURE:
<221> NAME/KEY: MOD_RES
<222> LOCATION: (11)
<223> OTHER INFORMATION: Variable amino acid residue

<400> SEQUENCE: 24

Leu Ile Arg Leu Cys Ser Xaa Ala Glu Gly Xaa Leu Glu Ala His Tyr
 1               5                  10                  15

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (7)
<223> OTHER INFORMATION: Variable amino acid residue

<400> SEQUENCE: 25

Pro Leu Asp His Leu Gly Xaa Phe Pro Tyr
 1               5                  10

<210> SEQ ID NO 26
<211> LENGTH: 13
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (4)
<223> OTHER INFORMATION: Variable amino acid residue

<400> SEQUENCE: 26

Val Ala Phe Xaa Gly Ser Gly Pro Leu Pro Phe Ser Ser
 1               5                  10

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: Synthetic
      consensus sequence

<400> SEQUENCE: 27

Asp Val Val Phe Leu Ala Ala Leu Val Gly Met
 1               5                  10

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
```

```
            consensus sequence
<220> FEATURE:
<221> NAME/KEY: MOD_RES
<222> LOCATION: (5)
<223> OTHER INFORMATION: Variable amino acid residue
<220> FEATURE:
<221> NAME/KEY: MOD_RES
<222> LOCATION: (10)
<223> OTHER INFORMATION: Variable amino acid residue

<400> SEQUENCE: 28

Arg Gly Gly Phe Xaa Val Leu Ala Val Xaa His Pro
  1               5                  10

<210> SEQ ID NO 29
<211> LENGTH: 328
<212> TYPE: PRT
<213> ORGANISM: Artificial Sequence
<220> FEATURE:
<223> OTHER INFORMATION: Description of Artificial Sequence: Synthetic
      amino acid sequence of nicotianamine synthase
<220> FEATURE:
<221> NAME/KEY: MOD_RES
<222> LOCATION: (1)..(10)
<223> OTHER INFORMATION: Variable amino acid residue
<220> FEATURE:
<221> NAME/KEY: MOD_RES
<222> LOCATION: (12)..(13)
<223> OTHER INFORMATION: Variable amino acid residue
<220> FEATURE:
<221> NAME/KEY: MOD_RES
<222> LOCATION: (16)..(21)
<223> OTHER INFORMATION: Variable amino acid residue
<220> FEATURE:
<221> NAME/KEY: MOD_RES
<222> LOCATION: (23)..(24)
<223> OTHER INFORMATION: Variable amino acid residue
<220> FEATURE:
<221> NAME/KEY: MOD_RES
<222> LOCATION: (26)..(27)
<223> OTHER INFORMATION: Variable amino acid residue
<220> FEATURE:
<221> NAME/KEY: MOD_RES
<222> LOCATION: (29)..(29)
<223> OTHER INFORMATION: Variable amino acid residue
<220> FEATURE:
<221> NAME/KEY: MOD_RES
<222> LOCATION: (31)..(36)
<223> OTHER INFORMATION: Variable amino acid residue
<220> FEATURE:
<221> NAME/KEY: MOD_RES
<222> LOCATION: (39)..(40)
<223> OTHER INFORMATION: Variable amino acid residue
<220> FEATURE:
<221> NAME/KEY: MOD_RES
<222> LOCATION: (43)..(44)
<223> OTHER INFORMATION: Variable amino acid residue
<220> FEATURE:
<221> NAME/KEY: MOD_RES
<222> LOCATION: (46)..(46)
<223> OTHER INFORMATION: Variable amino acid residue
<220> FEATURE:
<221> NAME/KEY: MOD_RES
<222> LOCATION: (48)..(51)
<223> OTHER INFORMATION: Variable amino acid residue
<220> FEATURE:
<221> NAME/KEY: MOD_RES
<222> LOCATION: (54)..(60)
<223> OTHER INFORMATION: Variable amino acid residue
<220> FEATURE:
<221> NAME/KEY: MOD_RES
<222> LOCATION: (62)..(62)
<223> OTHER INFORMATION: Variable amino acid residue
<220> FEATURE:
<221> NAME/KEY: MOD_RES
<222> LOCATION: (65)..(66)
<223> OTHER INFORMATION: Variable amino acid residue
```

```
<220> FEATURE:
<221> NAME/KEY: MOD_RES
<222> LOCATION: (69)..(70)
<223> OTHER INFORMATION: Variable amino acid residue
<220> FEATURE:
<221> NAME/KEY: MOD_RES
<222> LOCATION: (72)..(73)
<223> OTHER INFORMATION: Variable amino acid residue
<220> FEATURE:
<221> NAME/KEY: MOD_RES
<222> LOCATION: (76)..(77)
<223> OTHER INFORMATION: Variable amino acid residue
<220> FEATURE:
<221> NAME/KEY: MOD_RES
<222> LOCATION: (80)..(80)
<223> OTHER INFORMATION: Variable amino acid residue
<220> FEATURE:
<221> NAME/KEY: MOD_RES
<222> LOCATION: (82)..(85)
<223> OTHER INFORMATION: Variable amino acid residue
<220> FEATURE:
<221> NAME/KEY: MOD_RES
<222> LOCATION: (87)..(89)
<223> OTHER INFORMATION: Variable amino acid residue
<220> FEATURE:
<221> NAME/KEY: MOD_RES
<222> LOCATION: (91)..(91)
<223> OTHER INFORMATION: Variable amino acid residue
<220> FEATURE:
<221> NAME/KEY: MOD_RES
<222> LOCATION: (94)..(94)
<223> OTHER INFORMATION: Variable amino acid residue
<220> FEATURE:
<221> NAME/KEY: MOD_RES
<222> LOCATION: (97)..(98)
<223> OTHER INFORMATION: Variable amino acid residue
<220> FEATURE:
<221> NAME/KEY: MOD_RES
<222> LOCATION: (102)..(103)
<223> OTHER INFORMATION: Variable amino acid residue
<220> FEATURE:
<221> NAME/KEY: MOD_RES
<222> LOCATION: (106)..(107)
<223> OTHER INFORMATION: Variable amino acid residue
<220> FEATURE:
<221> NAME/KEY: MOD_RES
<222> LOCATION: (109)..(110)
<223> OTHER INFORMATION: Variable amino acid residue
<220> FEATURE:
<221> NAME/KEY: MOD_RES
<222> LOCATION: (113)..(114)
<223> OTHER INFORMATION: Variable amino acid residue
<220> FEATURE:
<221> NAME/KEY: MOD_RES
<222> LOCATION: (117)..(128)
<223> OTHER INFORMATION: Variable amino acid residue
<220> FEATURE:
<221> NAME/KEY: MOD_RES
<222> LOCATION: (131)..(131)
<223> OTHER INFORMATION: Variable amino acid residue
<220> FEATURE:
<221> NAME/KEY: MOD_RES
<222> LOCATION: (138)..(139)
<223> OTHER INFORMATION: Variable amino acid residue
<220> FEATURE:
<221> NAME/KEY: MOD_RES
<222> LOCATION: (141)..(142)
<223> OTHER INFORMATION: Variable amino acid residue
<220> FEATURE:
<221> NAME/KEY: MOD_RES
<222> LOCATION: (145)..(146)
<223> OTHER INFORMATION: Variable amino acid residue
<220> FEATURE:
<221> NAME/KEY: MOD_RES
<222> LOCATION: (149)..(152)
<223> OTHER INFORMATION: Variable amino acid residue
<220> FEATURE:
<221> NAME/KEY: MOD_RES
<222> LOCATION: (154)..(154)
```

-continued

```
<223> OTHER INFORMATION: Variable amino acid residue
<220> FEATURE:
<221> NAME/KEY: MOD_RES
<222> LOCATION: (156)..(161)
<223> OTHER INFORMATION: Variable amino acid residue
<220> FEATURE:
<221> NAME/KEY: MOD_RES
<222> LOCATION: (164)..(165)
<223> OTHER INFORMATION: Variable amino acid residue
<220> FEATURE:
<221> NAME/KEY: MOD_RES
<222> LOCATION: (167)..(168)
<223> OTHER INFORMATION: Variable amino acid residue
<220> FEATURE:
<221> NAME/KEY: MOD_RES
<222> LOCATION: (170)..(179)
<223> OTHER INFORMATION: Variable amino acid residue
<220> FEATURE:
<221> NAME/KEY: MOD_RES
<222> LOCATION: (182)..(182)
<223> OTHER INFORMATION: Variable amino acid residue
<220> FEATURE:
<221> NAME/KEY: MOD_RES
<222> LOCATION: (184)..(184)
<223> OTHER INFORMATION: Variable amino acid residue
<220> FEATURE:
<221> NAME/KEY: MOD_RES
<222> LOCATION: (186)..(194)
<223> OTHER INFORMATION: Variable amino acid residue
<220> FEATURE:
<221> NAME/KEY: MOD_RES
<222> LOCATION: (196)..(198)
<223> OTHER INFORMATION: Variable amino acid residue
<220> FEATURE:
<221> NAME/KEY: MOD_RES
<222> LOCATION: (206)..(206)
<223> OTHER INFORMATION: Variable amino acid residue
<220> FEATURE:
<221> NAME/KEY: MOD_RES
<222> LOCATION: (210)..(213)
<223> OTHER INFORMATION: Variable amino acid residue
<220> FEATURE:
<221> NAME/KEY: MOD_RES
<222> LOCATION: (215)..(219)
<223> OTHER INFORMATION: Variable amino acid residue
<220> FEATURE:
<221> NAME/KEY: MOD_RES
<222> LOCATION: (222)..(223)
<223> OTHER INFORMATION: Variable amino acid residue
<220> FEATURE:
<221> NAME/KEY: MOD_RES
<222> LOCATION: (226)..(227)
<223> OTHER INFORMATION: Variable amino acid residue
<220> FEATURE:
<221> NAME/KEY: MOD_RES
<222> LOCATION: (230)..(230)
<223> OTHER INFORMATION: Variable amino acid residue
<220> FEATURE:
<221> NAME/KEY: MOD_RES
<222> LOCATION: (232)..(238)
<223> OTHER INFORMATION: Variable amino acid residue
<220> FEATURE:
<221> NAME/KEY: MOD_RES
<222> LOCATION: (240)..(240)
<223> OTHER INFORMATION: Variable amino acid residue
<220> FEATURE:
<221> NAME/KEY: MOD_RES
<222> LOCATION: (245)..(245)
<223> OTHER INFORMATION: Variable amino acid residue
<220> FEATURE:
<221> NAME/KEY: MOD_RES
<222> LOCATION: (247)..(254)
<223> OTHER INFORMATION: Variable amino acid residue
<220> FEATURE:
<221> NAME/KEY: MOD_RES
<222> LOCATION: (257)..(257)
<223> OTHER INFORMATION: Variable amino acid residue
<220> FEATURE:
<221> NAME/KEY: MOD_RES
```

```
<222> LOCATION: (260)..(260)
<223> OTHER INFORMATION: Variable amino acid residue
<220> FEATURE:
<221> NAME/KEY: MOD_RES
<222> LOCATION: (262)..(262)
<223> OTHER INFORMATION: Variable amino acid residue
<220> FEATURE:
<221> NAME/KEY: MOD_RES
<222> LOCATION: (265)..(267)
<223> OTHER INFORMATION: Variable amino acid residue
<220> FEATURE:
<221> NAME/KEY: MOD_RES
<222> LOCATION: (269)..(269)
<223> OTHER INFORMATION: Variable amino acid residue
<220> FEATURE:
<221> NAME/KEY: MOD_RES
<222> LOCATION: (272)..(276)
<223> OTHER INFORMATION: Variable amino acid residue
<220> FEATURE:
<221> NAME/KEY: MOD_RES
<222> LOCATION: (278)..(328)
<223> OTHER INFORMATION: Variable amino acid residue

<400> SEQUENCE: 29

Xaa Xaa Xaa Xaa Xaa Xaa Xaa Xaa Xaa Xaa Leu Xaa Xaa Lys Ile Xaa
 1               5                  10                  15

Xaa Xaa Xaa Xaa Xaa Ile Xaa Xaa Leu Xaa Xaa Leu Xaa Pro Xaa Xaa
             20                  25                  30

Xaa Xaa Xaa Xaa Leu Phe Xaa Xaa Leu Val Xaa Xaa Cys Xaa Pro Xaa
         35                  40                  45

Xaa Xaa Xaa Asp Val Xaa Xaa Xaa Xaa Xaa Xaa Gln Xaa Met Arg
     50                  55                  60

Xaa Xaa Leu Ile Xaa Xaa Cys Xaa Xaa Ala Glu Xaa Xaa Leu Glu Xaa
 65                  70                  75                  80

His Xaa Xaa Xaa Xaa Leu Xaa Xaa Xaa Asp Xaa Pro Leu Xaa His Leu
                 85                  90                  95

Xaa Xaa Phe Pro Tyr Xaa Xaa Asn Tyr Xaa Xaa Leu Xaa Xaa Leu Glu
            100                 105                 110

Xaa Xaa Leu Leu Xaa Xaa Xaa Xaa Xaa Xaa Xaa Xaa Xaa Xaa Xaa Xaa
        115                 120                 125

Ala Phe Xaa Gly Ser Gly Pro Leu Pro Xaa Xaa Ser Xaa Xaa Leu Ala
    130                 135                 140

Xaa Xaa His Leu Xaa Xaa Xaa Xaa Phe Xaa Asn Xaa Xaa Xaa Xaa Xaa
145                 150                 155                 160

Xaa Ala Asn Xaa Xaa Ala Xaa Xaa Leu Xaa Xaa Xaa Xaa Xaa Xaa Xaa
                165                 170                 175

Xaa Xaa Xaa Arg Met Xaa Phe Xaa Thr Xaa Xaa Xaa Xaa Xaa Xaa Xaa
            180                 185                 190

Xaa Xaa Leu Xaa Xaa Xaa Asp Val Val Phe Leu Ala Ala Xaa Val Gly
        195                 200                 205

Met Xaa Xaa Xaa Xaa Lys Xaa Xaa Xaa Xaa His Leu Xaa Xaa His
    210                 215                 220

Met Xaa Xaa Gly Ala Xaa Leu Xaa Xaa Xaa Xaa Xaa Xaa Arg Xaa
225                 230                 235                 240

Phe Leu Tyr Pro Xaa Val Xaa Xaa Xaa Xaa Xaa Xaa Xaa Gly Phe
            245                 250                 255

Xaa Val Leu Xaa Val Xaa His Pro Xaa Xaa Val Xaa Asn Ser Xaa
        260                 265                 270

Xaa Xaa Xaa Xaa Lys Xaa Xaa Xaa Xaa Xaa Xaa Xaa Xaa Xaa Xaa
        275                 280                 285
```

```
Xaa Xaa Xaa Xaa Xaa Xaa Xaa Xaa Xaa Xaa Xaa Xaa Xaa Xaa
    290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa
            325

<210> SEQ ID NO 30
<211> LENGTH: 19
<212> TYPE: PRT
<213> ORGANISM: Hordeum vulgare

<400> SEQUENCE: 30

Asp Ala Gln Asn Lys Glu Val Ala Ala Leu Ile Glu Lys Ile Ala Gly
  1               5                  10                  15

Ile Gln Ala

<210> SEQ ID NO 31
<211> LENGTH: 7
<212> TYPE: PRT
<213> ORGANISM: Hordeum vulgare

<400> SEQUENCE: 31

Arg Glu Ala Leu Ile Arg Leu
  1               5

<210> SEQ ID NO 32
<211> LENGTH: 71
<212> TYPE: PRT
<213> ORGANISM: Oryza sativa

<400> SEQUENCE: 32

Met Glu Ala Gln Asn Gln Glu Val Ala Ala Leu Val Glu Lys Ile Ala
  1               5                  10                  15

Gly Leu His Ala Ala Ile Ser Lys Leu Pro Ser Leu Ser Pro Ser Ala
                 20                  25                  30

Glu Val Asp Ala Leu Phe Thr Asp Leu Val Thr Ala Cys Val Pro Ala
             35                  40                  45

Ser Pro Val Asp Val Ala Lys Leu Gly Pro Glu Ala Gln Ala Met Arg
     50                  55                  60

Glu Glu Leu Ile Arg Leu Cys
 65                  70

<210> SEQ ID NO 33
<211> LENGTH: 111
<212> TYPE: PRT
<213> ORGANISM: Oryza sativa

<400> SEQUENCE: 33

Tyr Val Asn Leu Ser Lys Leu Glu Tyr Asp Leu Leu Val Arg Tyr Val
  1               5                  10                  15

Pro Gly Ile Ala Pro Thr Arg Val Ala Phe Val Gly Ser Gly Pro Leu
                 20                  25                  30

Pro Phe Ser Ser Leu Val Leu Ala Ala His His Leu Pro Asp Ala Val
             35                  40                  45

Phe Asp Asn Tyr Asp Arg Cys Gly Ala Ala Asn Glu Arg Ala Arg Arg
     50                  55                  60

Leu Phe Arg Gly Ala Asp Glu Gly Leu Gly Ala Arg Met Ala Phe His
 65                  70                  75                  80
```

```
Thr Gly Asp Val Ala Thr Leu Thr Gly Glu Leu Gly Ala Tyr Asp Val
                85                  90                  95

Val Phe Leu Ala Thr Leu Val Gly Met Ala Ala Glu Glu Lys Pro
            100                 105                 110
```

<210> SEQ ID NO 34
<211> LENGTH: 64
<212> TYPE: PRT
<213> ORGANISM: Hordeum vulgare

<400> SEQUENCE: 34

```
Ser Phe His Thr Ala Asp Val Ala Asp Leu Thr Gln Glu Leu Gly Ala
1               5                   10                  15

Tyr Asp Val Val Phe Leu Ala Ala Leu Val Asp Met Ala Ala Glu Glu
            20                  25                  30

Lys Ala Lys Val Ile Ala His Leu Gly Ala His Met Val Glu Gly Ala
            35                  40                  45

Ser Leu Val Val Tyr Ser Ala His Gly Ala Arg Gly Phe Leu Tyr Pro
        50                  55                  60
```

<210> SEQ ID NO 35
<211> LENGTH: 19
<212> TYPE: PRT
<213> ORGANISM: Hordeum vulgare

<400> SEQUENCE: 35

```
Ala Phe His Thr Ala Glu Val Thr Asp Leu Thr Ala Glu Leu Gly Ala
1               5                   10                  15

Tyr Asp Val
```

<210> SEQ ID NO 36
<211> LENGTH: 29
<212> TYPE: PRT
<213> ORGANISM: Hordeum vulgare

<400> SEQUENCE: 36

```
Ala Asp Gly Ala Val Leu Val Ala Arg Ser Ala His Gly Ala Arg Ala
1               5                   10                  15

Phe Leu Tyr Pro Val Val Glu Leu Asp Asp Val Gly Arg
            20                  25
```

<210> SEQ ID NO 37
<211> LENGTH: 20
<212> TYPE: PRT
<213> ORGANISM: Hordeum vulgare

<400> SEQUENCE: 37

```
Pro Glu Asp Ile Arg Arg Gly Gly Phe Glu Val Leu Ala Val His His
1               5                   10                  15

Pro Glu Gly Glu
            20
```